(12) United States Patent
Latasa Osta

(10) Patent No.: US 11,242,521 B2
(45) Date of Patent: Feb. 8, 2022

(54) **OBTAINMENT OF A ROUGH-TYPE *SALMONELLA ENTERITIDIS* AND ITS GENETIC MODIFICATIONS FOR USE AS AN AVIAN VACCINE**

(71) Applicant: FARMACOLOGICOS VETERINARIOS S.A.C.—FARVET, C. P. (PE)

(72) Inventor: Cristina Latasa Osta, Multiva Navarra (ES)

(73) Assignee: FARMACOLOGICOS VETERINARIOS S.A.C.—FARVET

( * ) Notice: Subject to any disclaimer, the term of this patent is extended or adjusted under 35 U.S.C. 154(b) by 133 days.

(21) Appl. No.: 16/491,765

(22) PCT Filed: Jun. 12, 2018

(86) PCT No.: PCT/PE2018/000014
§ 371 (c)(1),
(2) Date: Sep. 6, 2019

(87) PCT Pub. No.: WO2018/231078
PCT Pub. Date: Dec. 20, 2018

(65) Prior Publication Data
US 2020/0370034 A1    Nov. 26, 2020

(30) Foreign Application Priority Data

Jun. 12, 2017 (PE) .................. 000992-2017/DIN

(51) Int. Cl.
| | |
|---|---|
| *A61K 39/04* | (2006.01) |
| *A61K 39/12* | (2006.01) |
| *C07H 21/02* | (2006.01) |
| *C12N 15/10* | (2006.01) |
| *C12N 1/20* | (2006.01) |
| *C12N 15/90* | (2006.01) |

(52) U.S. Cl.
CPC ............. *C12N 15/102* (2013.01); *C12N 1/20* (2013.01); *C12N 15/902* (2013.01); *C12N 2500/34* (2013.01)

(58) Field of Classification Search
CPC ........... A61K 39/04; A61K 39/12; C12N 1/00
USPC .......................... 424/93.1, 93.2, 93.4, 258.1
See application file for complete search history.

(56) References Cited

FOREIGN PATENT DOCUMENTS

| WO | WO 2009/013379 | 1/2009 |
|---|---|---|
| WO | WO 2009/065993 | 5/2009 |

OTHER PUBLICATIONS

Kong et al. "Effect of Deletion of Genes Involved in Lipopolysaccharide Core and O-Antigen Synthesis on Virulence and Immunogenicity of *Salmonella enterica* Serovar Typhimurium," Infection and Immunity, Oct. 2011, vol. 79, No. 10, pp. 4227-4239.
Latasa et al. "Evaluation of a *Salmonella* Strain Lacking the Secondary Messenger C-di-GMP and RpoS as a Live Oral Vaccine," PLOS One, Aug. 2016, vol. 11, No. 8, e0161216, 22 pages.
International Search Report for International (PCT) Patent Application No. PCT/PE2018/000014, dated Dec. 12, 2018, 3 pages.

*Primary Examiner* — Rodney P Swartz
(74) *Attorney, Agent, or Firm* — Sheridan Ross P.C.

(57) ABSTRACT

The present invention relates to a strain of *Salmonella enteritidis* 3934vac, which has been deleted the *waaL* gene to obtain a rough phenotype (3934vac *DwaaL*), the obtaining procedure and the oligos used with the objective of reducing toxicity and maintaining immunogenicity for its application as a vaccine. Another aspect of the present invention relates to a strain of *Salmonella enteritidis* 3934vac *DwaaL*, i.e. rough type, which has been modified to express the gene of the avian adenovirus type I fiber, in addition to the procedure for obtaining a *Salmonella enteritidis* 3034 vac *DwaaL* strain expressing an AvA-I fiber gene. The invention also comprises the development of a new, live, recombinant, effective and innocuous avian vaccine against the AvA-I virus developed via an insertion and integration process of AvA-I fiber genes in the chromosome of an attenuated and non-pathogenic strain of the bacterium *Salmonella enteritidis*.

Figure 2:
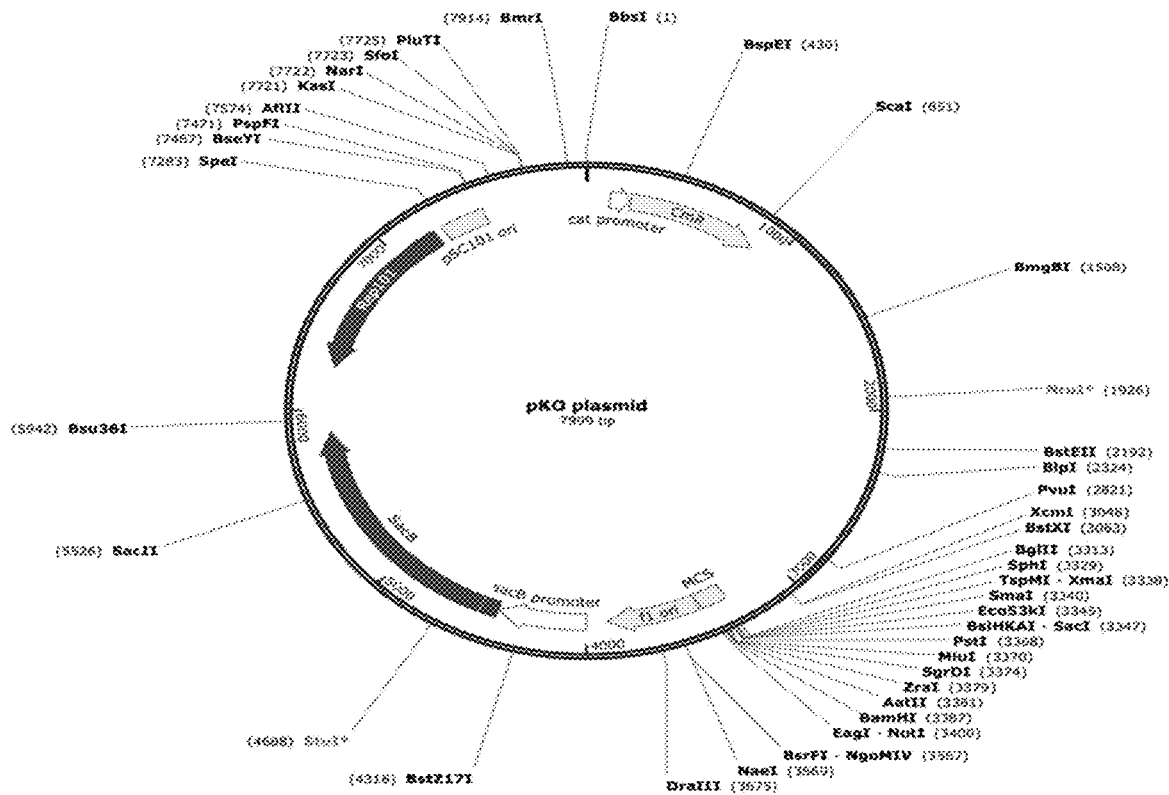

8 Claims, 8 Drawing Sheets
Specification includes a Sequence Listing.

FIGURE 1
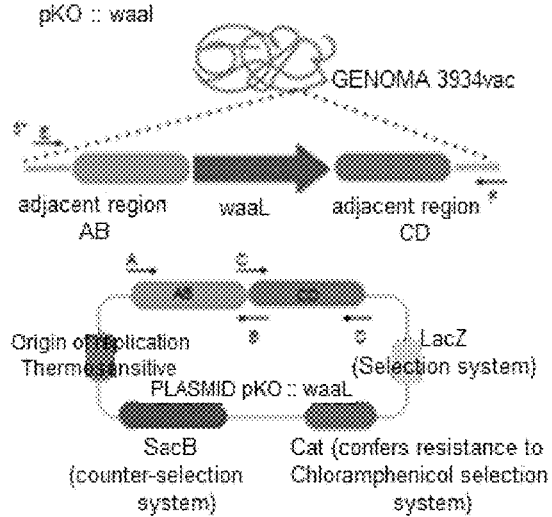
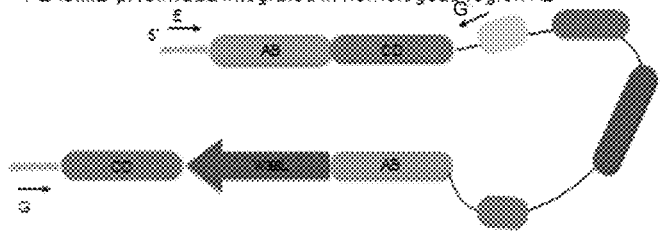
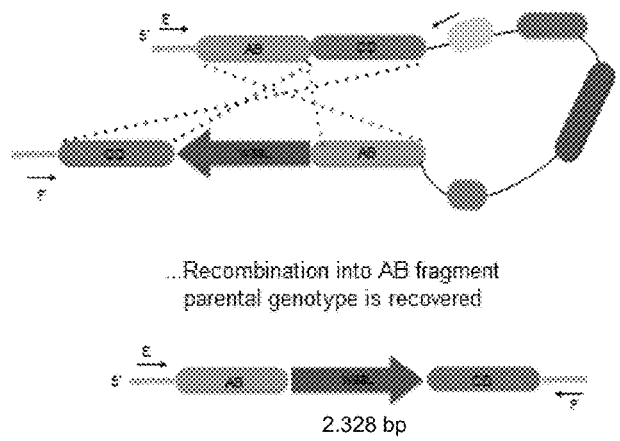

FIGURE 6

1- Construction and transformation of plasmid pKO :: ab13

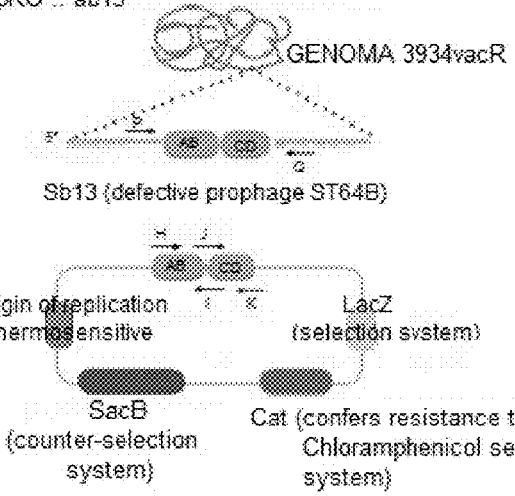

Sb13 (defective prophage ST64B)

Origin of replication Thermosensitive
LacZ (selection system)
SacB (counter-selection system)
Cat (confers resistance to Chloramphenicol selection system)

2- Assembly of expression cassette

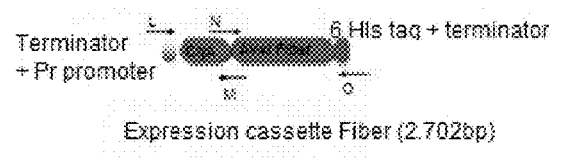

Expression cassette Fiber (2.702bp)

3- Construction and transformation of plasmid pKO :: ab13-Fiber

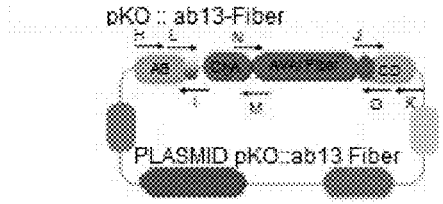

PLASMID pKO::ab13 Fiber

4- First and second recombination

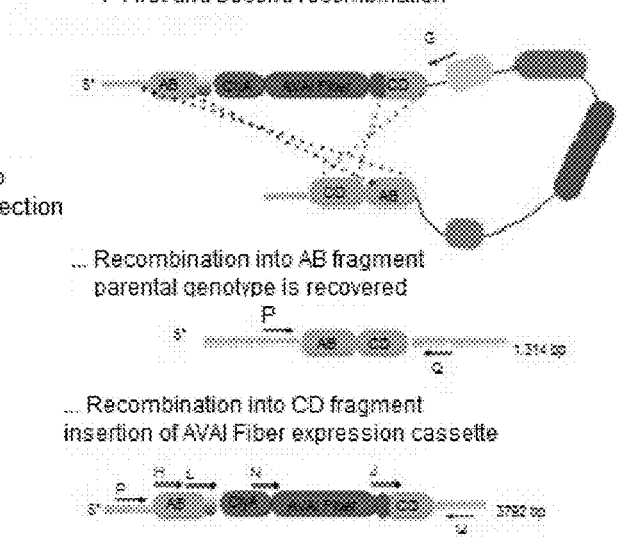

... Recombination into AB fragment parental genotype is recovered

... Recombination into CD fragment insertion of AVAI Fiber expression cassette

FIGURE 7

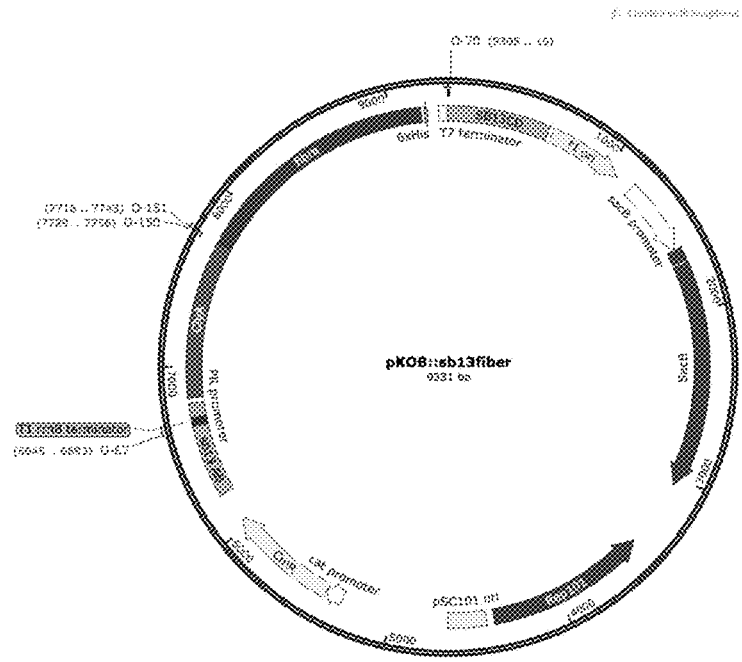

1- Salmonella wild strain
2- 3934vac
3- 3934vac -fiber
4- 3934vacDwood (rough mutant)
5- 3934vacDwood-fiber TSI: Triple Sugar Iron Agar; LIA: Lysine Iron Agar

FIGURE 14

| Oligo | Specificity | Sequence (5'-3') | Amplicon |
|---|---|---|---|
| A | rfaC | GCGGCCGCGCGATTATGCCATCGCAA | 520bp |
| B | Ig region rfaC – rfaL | CTCGAGTCCACAATAGGTTTGGGAT | |
| C | Ig region rfaL – rfaK | GTCGAGCGCTGATACTTATTACGG | 504bp |
| D | rfaK | AGATCTAAGCCGCAAGGGTGAAAA | |
| E | rfaC | TGGGATACGATAAACCGC | 2328 bp parental |
| F | rfaK | GCTTTTGCAGGCGTTCAA | 1106 bp mutant |
| G | Pko plasmid | CTCCGTAACAAATTGAGGAT | 1282bp (with oligo E) |
| H | Sb12 | CCCGGGAACTGTATGTCATTGCCGTA | 427 bp |
| I | Sb13 | GCATGCCCGATATAATCGAACGGCT | |
| J | Sb13 | GCATGCAGACGCCTGCTGATGAACT | 597 bp |
| K | Sb14 | GTCGACTGCAGACGGAACTGGTTA | |
| L | SYNTHETIC FRAGMENT | TTCGATTATATCGGGCATGCTAAAACGAAAGGCTCAGTCGAAAGACTGG | 1099 bp |
| M | SYNTHETIC FRAGMENT | GGAGCATGACGTCAGGAACCTCGAAAAG | |
| N | pET28::fiber | CTGACGTCATGCTCCGGGCCCCTAAAG | |
| O | pET28::fiber | TCAGCAGGCGTCTGCATGCCAAAAAACCCCCTCAAGACCCGT | 1618 bp |
| P | Sb12 | ATCGGTTGATTATGCCCGTCA | 1314 bp parental |
| Q | Sb14 | CAACACATAAGCACTGGTAT | 3792 bp strain with insertion |

OBTAINMENT OF A ROUGH-TYPE *SALMONELLA ENTERITIDIS* AND ITS GENETIC MODIFICATIONS FOR USE AS AN AVIAN VACCINE

CROSS REFERENCE TO RELATED APPLICATIONS

This application is a national stage application under 35 U.S.C. 371 and claims the benefit of PCT Application No. PCT/PE2018/000014 having an international filing date of 12 Jun. 2018, which designated the United States, which PCT application claimed the benefit of Peru Application No. 000992-2017/DIN filed 12 Jun. 2017, the disclosure of each of which are incorporated herein by reference.

REFERENCE TO SEQUENCE LISTING

This application contains a Sequence Listing submitted as an electronic text file named "20210617-SeqList.txt", having a size in bytes of 63 KB, and created on 17 Jun. 2021. The information contained in this electronic file is hereby incorporated by reference in its entirety pursuant to 37 CFR § 1.52(e)(5).

SECTOR OF THE TECHNIQUE

The present invention falls within the field of Animal Health. More specifically, the invention relates to the development of a strain of attenuated and rough-phenotype *Salmonella enterica* serovar *Enteritidis* (*Salmonella enteritidis* or SE), obtained by deletion of a gene involved in the synthesis of lipopolysaccharide. In this context, it also includes the use of this strain as a vaccine vector against the AvA-I virus (Aviadenovirus serogroup 1), via a process of insertion and integration into its chromosome of the genes that encode the AvA-I fiber antigen. The SE vector that is used has been genetically modified to function as a vehicle for the expression of the immunodominant genes of AvA-I virus fiber, with the goal of stimulating an effective and lasting immune response against HCI (viral hepatitis by body inclusion) in birds. The strain generated is completely safe because it is free of the twelve genes encoding the proteins of the signaling pathway of the secondary cyclic di-GMP messenger, the sigma RpoS factor and the WaaL protein. Therefore, this strain is proposed as a new effective and safe recombinant live vaccine against the AvA-I virus, suitable to vaccinate avian populations.

All the components of this vaccine have been specifically designed and developed with the three successive priority factors of efficacy, safety and costs.

BACKGROUND OF THE INVENTION

A growth of 30% is expected in the poultry sector for the next 8 to 10 years; this growth is accompanied by successful health programs, which in turn depend on effective and safe vaccines. HCI/SHP (inclusion body hepatitis/hepatitis hydropericardium syndrome) is a disease that causes up to 50% mortality in affected birds and is a latent problem in Peru, because despite the vaccination there are still outbreaks, a problem that is not solved because the technology used for the elaboration of vaccines is the same for 20 years.

Recently, the techniques of genetic manipulation, added to the availability of bacterial genomes, the better knowledge of the mechanisms of pathogenesis and the immune response have allowed new approaches for the development of attenuated bacterial strains as vectors of heterologous genes. Thus, enteropathogenic bacteria, such as *Listeria monocytogenes, Salmonella* spp, *Shigella* spp, *Vibrio cholerae, Yersinia enterocolitica* or *Bordetella pertussis* have been used as effective vectors as vaccines. Of all of them, *Salmonella* spp has given the most promising results. Thus, vaccine vectors based on attenuated *Salmonella typhimurium* strains have been used to generate a protective immune response against viral, bacterial and protozoan pathogens and as vehicle to carry anti-cancer treatments. In the specific case of birds, this type of vaccine has been evaluated as a gene vector for infectious bronchitis virus, avian influenza virus, avian reovirus and *Clostridium perfringens*. All these works agree with the fact that these vaccines were able to provoke a lasting protective immune response, besides being safe to avoid the risk of causing the disease. Considering the aspects mentioned above, there is a great support in the success that the development of a recombinant live vaccine against AvA-I using as a vector an attenuated SE strain would offer the poultry industry. These advantages can be summarized as follows: (1) severe attenuation through several processes of directed mutagenesis through a mechanism of allelic exchange that prevents reversion, do not introduce exogenous DNA and convert the resulting strain into a totally safe vaccine vector; (2) the amount of expression of the AvA-I antigen can be regulated by genetic manipulation; (3) it can be administered by oral inoculation; (4) it strongly stimulates the innate and adaptive immune system; and, (5) in turn, it would provide protection against SE. Although the development of vaccines using bacterial vectors has been and is currently the object of numerous investigations, to date there are no licensed commercial vaccines based on SE. Therefore, the development of this vaccine would set a good precedent in this area of research and development and would not have competition in national and international market.

The strain used in the present invention was isolated and described by Solano, C., Garcia, B. Valle, J., Berasain, C. Chigo J. M., Gamazo, C., & Lasa, I. Genetic Analysis of *Salmonella enteritidis* biofilm formation: Critical role of cellulose. *Molecular Microbiology,* 43(3), pp. 793-808. This study reports a new screening method based on the fluorescence of colonies on calcofluor agar plates to identify mutants of *Salmonella enteritidis* that are defective in biofilm formation. These results not only confirmed the requirement of genes already described for the modulation of multicellular behavior in *Salmonella typhimurium* and other species but also revealed new aspects of the biofilm formation process, such as new genetic elements named as bcs-ABZC and bcsEFG operons, necessary for the synthesis of an exopolysaccharide hydrolysable by cellulase. Non-polar mutations of the BcsC and bcsE genes, as well as complementation experiments, demonstrated that both operons are essential for cellulose biosynthesis in the LB and ATM media, both in *S. enteritidis* and *S. typhimurium*. This study also showed that the biofilm produced by *S. enteritidis* is composed of different components, suggesting that the composition and regulation of the biofilm depends on environmental conditions. In addition, the results suggest that cellulose is not involved in the virulence of *S. enteritidis*, although mutants deficient in the production of this polysaccharide were more sensitive to chlorine treatments, suggesting that cellulose production and the formation of biofilm would be an important factor in the survival of *S. enteritidis* on surfaces. In a later study, Solano C., Garcia, B., Latasa, C. Toledo-Arana, A. Zorraquino, V. Valle, Joan Casals, Enrique Pedroso and Iñigo Lasa. Genetic Reductionist Approach for Dissecting Individual roles of GGDEF proteins within the c-di-GMP signaling network in *Salmonella. Proceedings of the National Academy of Sciences of the United States of America,* 106 (19, pp. 7997-8002. (2009) performed an ambitious genetic approach in which the 12 genes that encode proteins with enzymatic activity of diguanylate cyclase (DGC, proteins with GGDEF domain) were deleted in the same strain described above. These enzymes synthesize the secondary messenger c-di-GMP, a molecule whose involvement in key bacterial biological processes such as the formation of biofilms or virulence has been widely studied in numerous species. In the specific case of this strain of SE, the total depletion of c-di-GMP correlates with the loss of the capacity to form biofilms, a slight attenuation in a murine model and a greater sensitivity to extreme environmental conditions.

As a result of the genetic approach described above, patent document ES 2324084B1 describes the invention of a method that allows producing multiple modifications in the chromosome of Gram negative bacteria and strains of *Salmonella* deficient in synthesis of C-di-GMP obtained by it. Said invention also relates to two mutant strains of enteric *Salmonella* obtained by said method in which the twelve genes encoding proteins with GGDEF domain have been deleted (mutant ΔXII::Km and mutant ΔXII::Clo) and to the use thereof as expression vectors, immunotherapeutic agents and in metabolic studies.

Garcia Ona Enrique. "Análisis de una cepa avirulenta de *Salmonella enteriditis* para su use como vacuna viva atenuada. *Universidad Pública de Navarra* (2011), the Thesis: Analysis of an Avirulent Strain of *Salmonella enteritidis* for Use as Live Attenuated Vaccine, studied the potential of several derived strains included in document ES 2324084B1 for the development of a vaccine able to induce an immune response, decrease the colonization of organs and the release of *Salmonella* in feces in intensive pig farms. This work concluded that the candidate *Salmonella* strain for the development of a vaccine would be the strain known as S. *Enteritidis* 3934ΔXII*, which has deleted the 12 genes that encode proteins with GGDEF domain and carries an additional deletion in a chromosomal region that includes the transcriptional regulator RpoS. This strain is avirulent, has a diminished ability to survive in the environment and since it does not contain exogenous DNA, it would not be classified as GMO (genetically modified organism). Oral immunization assays using a murine infection model, revealed that immunization with a single dose of $10^7$ ufc (Colony Forming Units) of this strain is capable of inducing a protective immune response against *Salmonella* infection, indicating that strain may be a suitable candidate for use as a live attenuated vaccine.

Latasa, C., Echeverz, M., Garcia, B., Gil, C., Garcia-ona, E., Burgui, S. Noelita Caseres, S. Hervás-Stubss., J. J., Lasarte, I. Lasarte., C. Solano Evaluation of *Salmonella* strain lacking the secondary messenger c-di-GMP and Rpos as a live oral vaccine. *PLos ONE,* 11(8), pp. 1-22 (2016) conducted the following study with the objective of constructing a new live attenuated *Salmonella* vaccine: first, the impact of the absence of cyclic di-GMP (c-di-GMP) on the *Salmonella* virulence was analyzed. As previously mentioned, C-di-GMP is a secondary intracellular messenger that controls a wide range of bacterial processes, including the formation of biofilm and the synthesis of virulence factors, as well as modulating the innate immune response of the host through the STING receptors. The results described in this article showed that a multiple mutant of *Salmonella*, from whose genome the twelve genes encoding diguanylate cyclase proteins have been deleted and, as a consequence, cannot synthesize c-di-GMP, presents a moderate attenuation in a model of systemic murine infection. A further controlled mutation (unlike the *S. enteritidis* 3934ΔXII* strain, in which the loss of this sigma factor had resulted from a natural counter-selection) of the rpoS gene resulted in a synergistic attenuating effect, which led to a highly attenuated strain, called ΔXIII. This strain is sufficiently immunogenic to protect mice against an oral lethal attack of a virulent strain of *S. typhimurium*. The immunogenicity of ΔXIII depends both on the activation of the humoral and cellular response and is characterized by the production of opsonizing antibodies and the induction of significant levels of IFN-γ, TNF-A, IL-2, IL-17 and IL-10. ΔXIII is capable of forming biofilms and does not survive under desiccation conditions, which indicates that it could be easily removed from the environment. In addition, ΔXIII has DIVA (Differentiating Infected from Vaccinated Animals) properties, which allow the differentiation of infected and vaccinated animals. In order to facilitate the terminology, the ΔXIII strain is also known as 3934vac.

Additionally, the paper of Kong Q., Yang, J., Liu, Q., Alamuri, P., Roland, K. L. & Curtiss, R. Effect of Deletion of Genes Involved in Lipopolysaccharide Core and O-antigen synthesis on virulence and Immunogenicity of *Salmonella enterica serovar Typhimurium. Infection and Immunity,* 79(10), pp. 4227-4239. (2011), describes the effect of the elimination of the O-antigen and the sugars of the core in the virulence and immunogenicity of *Salmonella enterica* serotype *typhimurium*. In this study, non-polar mutations by deletion were performed in the waaG (rfaG), waaL (rfaI), rfaH, waaJ (rfaJ), wbaP (rfbP), waaL (rfaL), or wzy (rfc) genes in a wild-type strain of *S. typhimurium*. After confirming the structure of the LPS, several properties in vitro and in vivo of each mutant were analyzed and all mutants showed a significant attenuation and lower invasion capacity compared to the wild-type parental strains when administered to BALB/c mice orally. In addition, the strains carrying a mutation in waaG and waaL were deficient in the colonization of the Peyer patches and liver, this deficiency being partially compensated after the intranasal administration of the mutant DwaaL. In the context of an attenuated vaccine strain supplying the pneumococcal antigen PspA, all mutations tested resulted in reduced immune responses against PspA and *Salmonella* antigens. These results indicate that non-reversible truncation of the outer core is not a viable option to develop a live oral *Salmonella* vaccine, whereas a wzy mutant, which retains one unit of the O-antigen, would be adequate to stimulate optimal protective immunity to homologous or heterologous antigens orally, intranasally or intraperitoneally.

GENERAL DESCRIPTION OF THE INVENTION

The present invention relates to an attenuated *Salmonella enteritidis* strain that has been modified by genetic engineering techniques to delete the waaL gene and therefore has a rough phenotype. Another aspect of the present invention relates to said mutant *Salmonella enteritidis* strain in the waaL gene that also carries the genes encoding the AvA-I fiber antigen on its chromosome. This strain, apart from having a rough phenotype and being avirulent, confers protection against AvA-I. Additionally, the invention comprises the process for obtaining an attenuated *Salmonella enteritidis* strain with a rough phenotype and carrying out the integration of the genes encoding the AvA-I fiber into its chromosome, including the plasmids and methods used to obtain said strain.

With the aim of reducing the toxicity and maintaining the immunogenicity of the strains based on the 3934vac genetic background (SE ΔXIII), one aspect of the present invention relates to the deletion of the waaL gene. The mutation of this gene results in a rough phenotype because the lipopolysaccharide is composed only of the core and lipid A, having lost the ability to synthesize the O-antigen. This mutation has the additional advantage of allowing the differentiation of animals vaccinated and naturally colonized by wild-type strains of Salmonella enteritidis and typhimurium.

For the generation of the rough mutants, an experimental design based on an allelic exchange was used, which gives rise to a thermosensitive plasmid carrying two regions homologous to the adjacent 5 and 3' of the waaL gene. In order to carry out the allelic exchange by homologous recombination, two fragments of approximately 500 bp flanking waaL in the 3' and 5'-regions (fragments AB and CD) were first cloned into this plasmid. The constructed plasmid was introduced into the 3934vac strain by electroporation (the Salmonella strain carrying this plasmid is grown at 28° C. in the presence of 20 µg/mL chloramphenicol). After the strain was transformed, several clones were selected for the integration of the plasmid into the chromosome by cultivation at 42° C. (a non-permissive temperature for plasmid replication). After confirmation of the integration of the vector into the chromosome by PCR, it proceeded to excision or second recombination. In this second step, the plasmid is lost having generated the desired deletion or having restored the wild copy of the gene (the approximate ratio of these genetic events is 50-50%). The second recombination is achieved by cultivation at 30° C. in the absence of antibiotic and in the presence of sucrose, since the plasmid carries the lethal sacB gene and the presence of this sugar in the culture medium counter-selects the clones that still retain the plasmid. The confirmation of those clones in which the allelic exchange occurred was carried out by PCR and subsequent sequencing. It should be noted that the mutants resulting from this procedure do not carry resistance to antibiotics or traces of exogenous DNA.

In order to integrate an expression cassette into the chromosome that would allow the production of the fiber antigen in the SE strain, an approach similar to that previously described was carried out. In this case, the plasmid contains, apart from the recombination flanking regions, an expression cassette that is integrated into the chromosome. This expression cassette was cloned into an integrative plasmid carrying the AB and CD regions of approximately 500 bp of the Sb13 gene of the ST64B prophage. The cloning was designed so that the AvA-I fiber expression cassette is between both fragments of the defective prophage gene (the Salmonella strain carrying this plasmid is grown at 28° C. in the presence of 20 µg/mL chloramphenicol). Once the plasmid was transformed by electroporation, several clones were subjected to several growth passages at 42° C. (non-permissive temperature of plasmid replication—integration of the plasmid occurs thanks to the AB and CD homologous regions adjacent to waaL). After checking by PCR that the plasmid had integrated into the chromosome, excision or second recombination was carried out at 28° C. in the absence of antibiotic and presence of sucrose. As described above, this counter-selection system allows identifying clones that have lost in the plasmid. The last step consists again in selecting by PCR the clones in which the insertion of the fiber expression cassette in the sb13 gene of the prophage ST64B has occurred.

The resulting strain, to which this invention refers, is a modified mutant strain of Salmonella enteritidis that carries a deletion of the waaL gene, and therefore has a rough phenotype, and expresses AvA-I fiber genes from its own chromosome.

For purposes of the present invention, Salmonella enteritidis is an abbreviation of Salmonella enterica serovar Enteritidis.

In addition, for the present invention it should be considered that PCR is the polymerase chain reaction; and oligo is the primer used in PCR.

DETAILED DESCRIPTION OF THE INVENTION

Obtaining Attenuated Salmonella Enteritidis (ASE)
Design and Construction of a System that Allows the Introduction of any Xenoantigen of Interest in the Chromosome of Salmonella enteritidis (SE).

A live vaccine or vaccine vector must be safe and effective, with a genotype and phenotype fully controlled, that avoid the risk of reversion to virulence. In addition, the strain must maintain a balance between the degree of attenuation and immunogenicity, remaining in the host organism long enough to give rise to a protective immune response against homologous and/or heterologous antigens. In this case, the strain of avian Salmonella enteritidis (ASE) generated has as its main characteristics a drastic attenuation in birds. In addition, the ASE strain is unable to form biofilms and has a much lower survival in the environment, avoiding any risk associated with the period in which the vaccinated animals could excrete this strain. Unlike most commercial vaccines (such as 9R), its genotype and phenotype are fully controlled and do not possess antibiotic resistance genes. The safety of live attenuated bacteria has been verified in other models such as the 9R vaccine, whose reports scientifically ruled out a potential reversion to the original virulent form (Okamoto, A. S., Menconi, A., Goncalves, G A. M., Rocha, T. S., Andreatti Filho, R. F., Savano, E. N., & Sesti, L. *Revision to virulence evaluation of a 9R vaccine strain of Salmonella enterica serovar gallinarum in commercial brown layers*" Revista Brasileira de Ciencia Avicola, 12(1), pp. 47-52. 2010).

Therefore, the present invention uses a strain of Salmonella enteritidis 3934 (deposited in the Spanish Type Culture Collection (CECT) with the access number CECT 9333, to which, by genetic engineering techniques, the twelve genes encoding diguanylate cyclase enzymes, the rpoS gene and the waaL gene have been deleted. This last mutation was carried out with the aim of obtaining a vaccine strain of rough phenotype (Salmonella enteritidis 3934vac DwaaL) that confers protection in breeding animals. In addition, another aspect of the present invention comprises a vaccine strain of rough phenotype carrying an expression cassette for AvA-I fiber genes (Salmonella enteritidis 3934vac DwaaL-fiber) which confers immunity against inclusion body hepatitis in birds.

Generation of Rough Mutants

In order to reduce the toxicity and maintain the immunogenicity of the strains based on the 3934vac genetic background, it proceeded to delete the waaL gene. The mutation of this gene results in a rough phenotype because the lipopolysaccharide is composed only of core and lipid A, having lost the ability to synthesize the O-antigen. This mutation has the additional advantage of allowing the differentiation of vaccinated and naturally colonized animals by wild strains of *Salmonella enteritidis* and *typhimurium*.

Detailed Methodology

The methodology used is to construct an integrative vector pKO:waaL, integrate this vector pKO:waaL in a first step of recombination and then perform the excision of the integrative vector with a second step of recombination (FIG. 1)

1. Construction of the Integrative Vector pKO:waaL

For the construction of the integrative plasmid pKO::waaL, two flanking fragments to the waaL gene of 520 bp (oligonucleotides A and B) and 504 bp (oligonucleotides C and D), respectively, are amplified by PCR. The PCR products are purified from gel and cloned independently in standard cloning vectors, later to be digested to NotI XhoI (fragment AB) and XhoI BglII (fragment CD). Both digested fragments are purified from gel and subcloned in the pKO plasmid, whose sequence is SEQ ID NO:1 digested to NotI BIgII, giving rise to the vector pKO::waaL. The pKO plasmid carries a cassette of resistance to Chloramphenicol, a thermosensitive origin, lacZ selection system and sacB for counter-selection (FIG. 2)

The construction pKO::waaL, whose sequence is SEQ ID NO:2, is carried out in a strain of *Escherichia coli* and is verified by PCR, miniprep and digestion.

The Oligonucleotides used for the construction of the pDEST::waaL vector are shown in Table 1. Sequence (5'-3'). The restriction sites are underlined.

TABLE 1

Oligonucleotides used to perform the deletion of the waaL gene in *Salmonella enteritidis* 3934

| Name of the gene | Oligonucleotides |
| --- | --- |
| waaL | oligo A (SEQ ID NO: 3) |
|  | oligo B (SEQ ID NO: 4) |
|  | oligo C (SEQ ID NO: 5) |
|  | oligo D (SEQ ID NO: 6) |

2. Integration of the Suicide Vector pKO::waaL (First Recombination)

Figure 3:
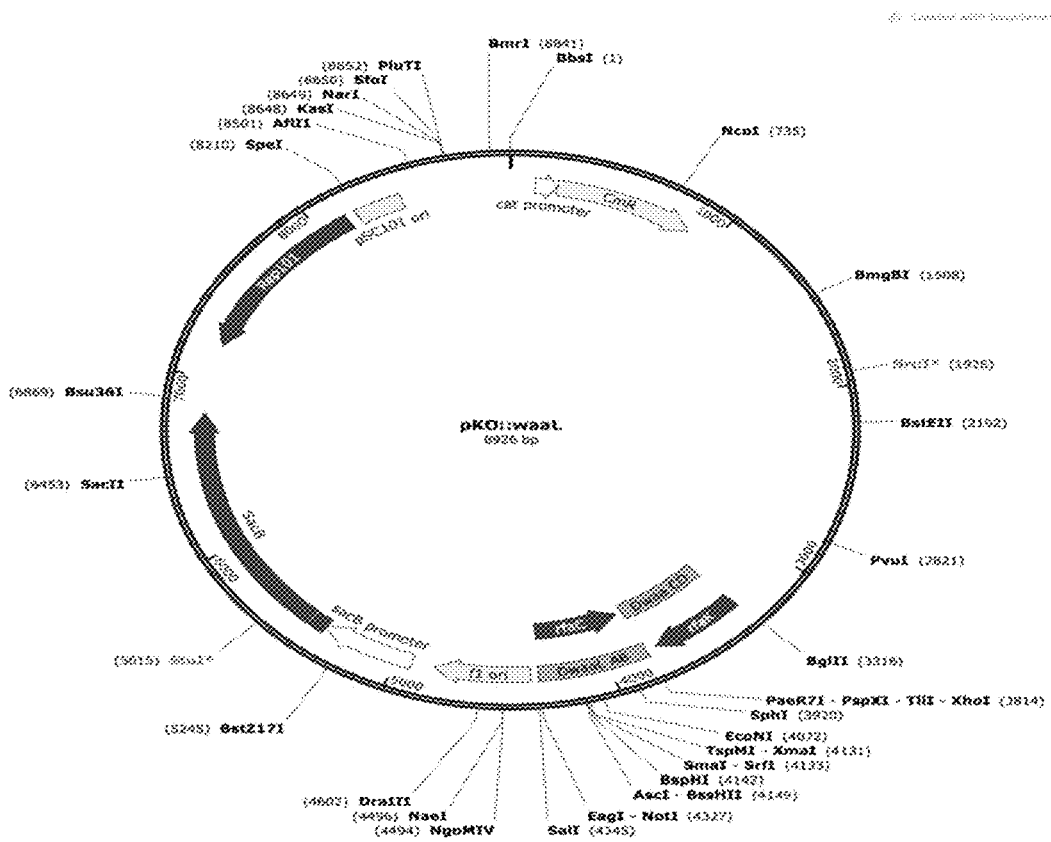
Figure 4:
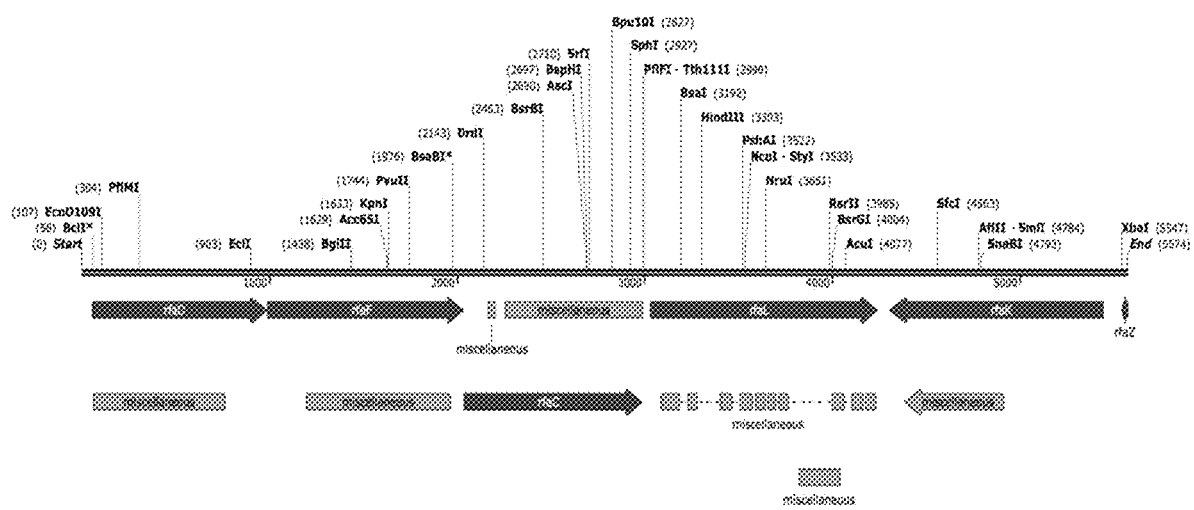
Figure 5:
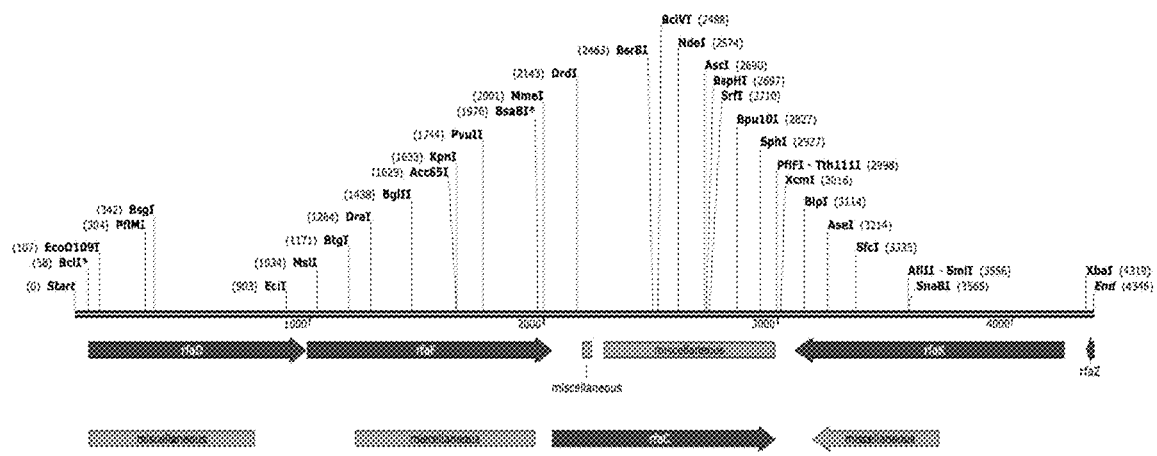
Figure 8:
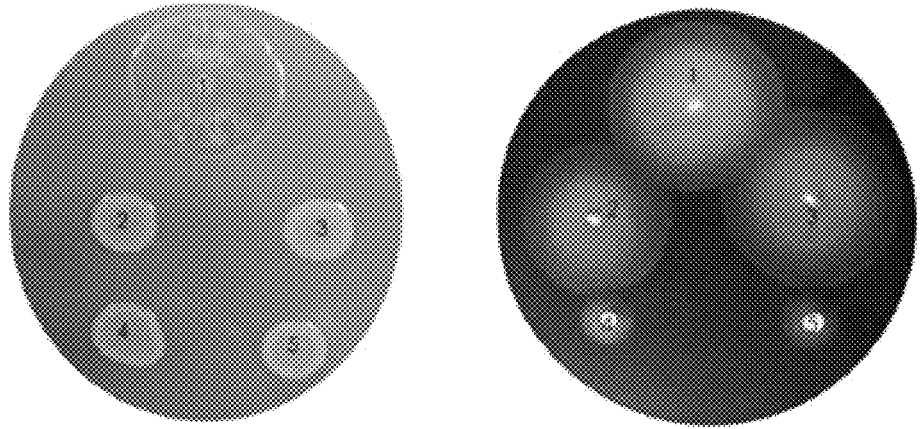
Figure 9:
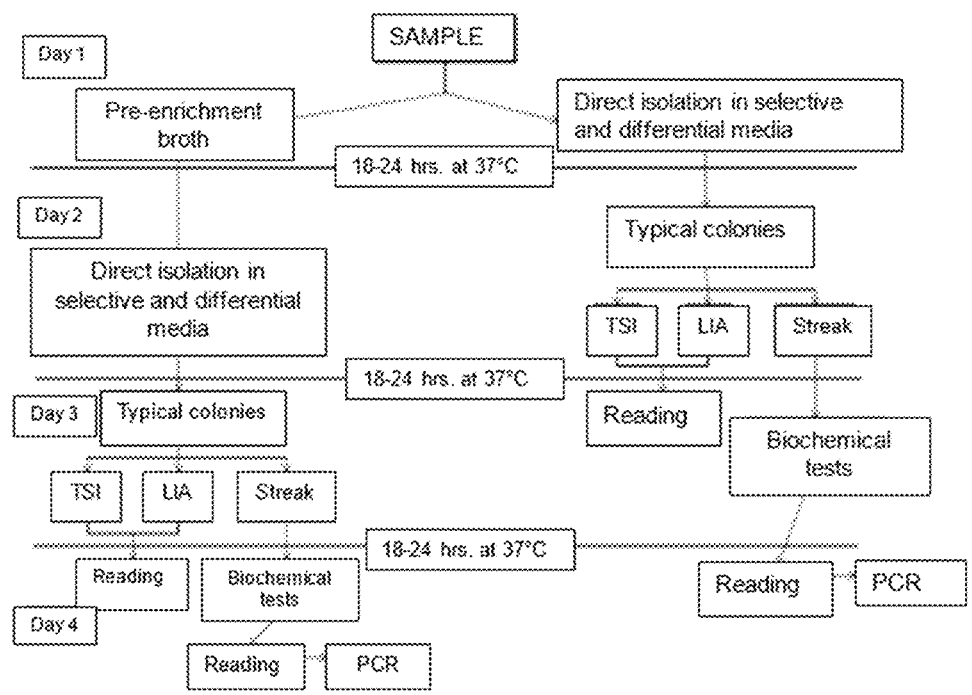

Once constructed and verified the pKO::waaL plasmid (FIG. 3), this is extracted from the strain of *Escherichia coli* by means of miniprep and is electroporated in the S. *Enteritidis* 3934vac strain, where its integration is forced by growth at 42° C. This temperature is not permissive for the replication of the plasmid and the integration of the plasmid occurs thanks to the homologous regions AB and CD adjacent to waaL. Several clones resulting from the incubation at 44° C., resistant to chloramphenicol, were tested by PCR with the pairs of oligos E-F and E-G to verify the integration. In the first case, the PCRs must be negative and in the second case, those clones in which the recombination took place in the AB fragment, the resulting PCR will be 1282 bp.

TABLE 2

Oligonucleotides used for the verification of the integration of the pKO::waaL plasmid

| Name of Oligo | Sequence |
|---|---|
| oligo E | SEQ ID NO: 9 |
| oligo F | SEQ ID NO: 10 |
| oligo G (hybridized in the pKO plasmid) | SEQ ID NO: 11 |

3. Excision of the Integrative Vector pKO::waaL (Second Recombination)

In order that the second recombination event occurs and the pKO plasmid is lost, several integrated clones are grown in liquid medium at 30° C. in the absence of antibiotic. After 24 hours, 5 serial dilutions are plated on solid medium supplemented with 5% sucrose. In this medium, only those clones that have lost the plasmid through a second recombination grow, depending on the fragment in which it has taken place, giving rise to the regeneration of the parental genotype or to the total deletion of the waaL gene. Both alleles can be differentiated by PCR with oligos E and F (sequence described above)

In the parental strain 3934vac, PCR with oligos E and F results in a fragment of 2328 bp, the sequence of the amplicon from genotype 3934vac is SEQ ID NO:7, whereas in clones in which the deletion has occurred, the fragment has a size of 1106 bp, whose amplicon sequence is SEQ ID NO:8

The 3934vacDwaal or 3934vacR strain can be grown at 37° C. in the absence of antibiotic, since it does not carry any selection cassette.

The Waa region (rfa) of *Salmonella enteritidis* 3934vac and the Waa region (rfa) of *Salmonella enteritidis* 3934vacR can be seen in FIG. 4 and FIG. 5, respectively.

The oligonucleotides used in the verification of the DwaaL mutants are: SEQ ID NO:9 and SEQ ID NO:10

Construction and Insertion of Cassette with AvA-I Fiber Genes in the 3934VacR Strain Construction and Insertion of Expression Cassette with AvA-I Fiber Genes in the Chromosome of 3934VacR.

The insertion of the genes of interest in the 3934vacR strain is carried out at the chromosomal level. This strategy allows the expression of heterologous genes to be stable, eliminating the problem of plasmid segregation and the need to use antibiotics as selection markers. The steps are summarized in FIG. 6.

1. Construction of the Integrative Vector pKO:Sb13-Fiber

In this first phase, an integrative plasmid is constructed to integrate the expression cassette in the sb13 gene of the defective prophage ST64B (All strains of SE have it in their chromosome) (FIG. 6). Following an approach similar to that described above, the AB (427 bp) and CD (597 bp) regions are amplified with the oligo pairs H-I and J-K. The PCR products are purified from gel and cloned independently in standard cloning vectors, later to be digested with SmaI sphI (fragment AB) and spHI SaII (fragment CD). Both digested fragments are purified from gel and subcloned in the suicide plasmid pKO digested to SmaI SaII, giving rise to the vector pKO::sb13 (FIG. 7) whose sequence is SEQ ID NO:12.

Oligos Used

Fragment AB:

oligo H (SEQ ID NO:13)

oligo I (SEQ ID NO:14)

Fragment CD:

oligo J (SEQ ID NO:15)

oligo K (SEQ ID NO:16)

Once the pKO::sb13 plasmid is constructed, the cassette is assembled, which will give rise to the expression of the fiber antigen. This step is carried out in several phases: (i) Amplification of <Terminator (43 bp)-Pr.promotor.RBS (114 bp)-clyA (915 bp)> from a synthetic plasmid with oligonucleotides L-M, (ii) amplification of the coding region of the fiber antigen (1597 bp) using as template the pET28::

fiber plasmid with the pair of oligonucleotides N-O, and (iii) overlapping PCR to fuse both fragments, with the external oligos L-O.
Oligo L (SEQ ID NO:17)
Oligo M (SEQ ID NO:18)
Oligo N (SEQ ID NO:19)
Oligo 0 (SEQ ID NO:20)
The fiber expression cassette has the sequence SEQ ID NO:21.

The resulting fragment (2,702 bp) is purified from gel and cloned by assembly of homologous ends in the vector pKO::sb13 previously digested to spHI, obtaining the vector pKO::sb13-Fiber, whose sequence is SEQ ID NO:22.

2. Integration of the Suicide Vector pKO::Sb13-Fiber (First Recombination)

Once constructed and verified, the pKO::sb13-fiber plasmid, this is extracted from the *Escherichia coli* strain by miniprep and electroporated into the *S. enteritidis* 3934vacR (or 3934vac DwaaL) strain, where its integration is forced by growth at 42° C. This temperature is not permissive for the replication of the plasmid and the integration of the plasmid occurs thanks to the homologous regions AB and CD homologous to the sb13 gene. Several clones resulting from incubation at 44° C., resistant to chloramphenicol, are tested by PCR with the pairs of oligos P-Q and P-M to verify the integration. In the first case, the PCRs must be negative and in the second case, those clones in which the recombination took place in the AB fragment, the resulting PCR will be 1607 bp.

The oligos used were:

Oligo P (SEQ ID NO:23)
Oligo Q (SEQ ID NO:24)
Oligo M (SEQ ID NO:25)

Excision of the Integrative Vector pKO::Sb13-Fiber (Second Recombination)

In order that the second recombination event occurs and the pKO plasmid is lost, leaving the fiber antigen expression cassette inserted into the chromosome, several integrated clones are grown in liquid medium at 30° C. in the absence of antibiotic. After 24 hours, 5 serial dilutions are plated on solid medium supplemented with 5% sucrose. Only those clones that have lost the plasmid through a second recombination grow in this medium, which, depending on the fragment in which it took place, results in the regeneration of the parental genotype or insertion in the sb13 gene of the defective prophage ST64B of the expression cassette responsible for the production of the fiber antigen. These latter clones can be differentiated by PCR, using the oligos P and Q (sequence described above).

In the parental strain 3934vacR, the PCR with oligos P and Q results in a fragment of 1314 bp, while in clones in which the 3934vacR::FIBER (AvA-I) strain has been produced, the integration of the fiber expression cassette has a size of 3792 bp bp.

The sequence in the genetic background 3934vacR is SEQ ID NO:25.

The sequence sb13 in genetic background 3934vacR::FIBER (AvA-I) is SEQ ID NO:26.

Detection of the Expression of Fiber Proteins by ASE

For the confirmation of the heterologous expression of the fiber antigen, the SDS-PAGE and Western blot techniques are used. The heterologous proteins are expressed by culturing the bacteria in LB medium, then proteins are extracted from the cytoplasm, periplasm and secreted. The samples obtained from the expression are separated by SDS-PAGE in 10% polyacrylamide gels. The proteins are transferred to nitrocellulose membranes and the proteins are detected indirectly using IgG-HRP (antibody linked to horseradish peroxidase) as conjugate, followed by detection using DAB (3,3' Diaminobenzidine tetrahydro chloride) as substrate.

Thus, the results obtained by Western blot validate and satisfactorily corroborate the expression of the fiber antigen in the *Salmonella enteritidis* 3934Vac strain under both 37° C. and 28° C. growth conditions. While none of the bands (A, B, and C) match exactly the estimated theoretical molecular weight of the ClyA-FiberAvAI-His fusion (85.4 kDa), band A probably matches the full size of the fusion, while the bands B and C are products of protein degradation. Where ClyA represents the sequence of the ClyA gene; fiberAvAI represents the fiber gene sequence of AvA-I and His represents the sequence of 6 consecutive histidines.

Phenotypic Study of 3934 Strains and Rough Vaccine Derivatives.

In order to study the phenotypes of the different strains, they were plated on Congo red agar, which allowed to differentiate in a simple way the strain of *Salmonella* that carries the fiber gene. Unlike wild strains, which normally produce cellulose, fimbriae and other appendages, giving rise to the RDAR—red, dry and rough genotype, the mutants generated in the present invention have a phenotype known as saw (smooth and white). This phenotype is especially noticeable when the strains produce a truncated lipopolysaccharide, due to the mutation in waaL gene. The differences are also significant in semisolid swimming agar, although this phenotype may suffer variations depending on the exact composition and humidity of the culture plates (FIG. 8).

Evaluation of Recombinant Vaccine

Immunization and Challenge Tests

Preparation of the Inoculum of the Vaccine.

The inoculum is prepared from the RAvA-SE strain that adequately expresses the AvA-I fiber gene. The bacterium is plated in XLD medium and incubated for 24 hours at 37° C. Typical colonies are transferred to LB medium, culture is incubated for 18 hrs at 37° C. under stirring at 250 rpm (mechanical stirrer). Bacterial cells are collected by centrifugation at 5000 g for 10 min and serially diluted in PBS according to the desired concentration.

Preparation of the AvA-I Inoculum for Challenge Tests.

The AvA-I isolation used in the trial was obtained from an outbreak of HCI (inclusion body hepatitis) from a farm in Chincha, Ica, Peru, characterized as AvA-I serotype 4 by RFLP-PCR. The isolate is inoculated in 10-day-old SPF eggs through the chorioallantoic membrane (CAM) and incubated for 9 days, after which the livers are collected to be homogenized and the viral load is determined by PCR. The mean infective dose in chicken embryo (IDCE 50/mL) of the inoculum is calculated using the formula of Reed and Muench. The homogenized material is stored at −20° C. until its use in the challenge.

Protection Test

At this point, the animal tests will allow evaluating the immunogenicity of the candidate vaccine RAvA-SE. To do this, a similar schedule is established as shown below. The number of groups to work is established according to the dose and route of administration. If more than one candidate vaccine is generated, the same scheme will also be followed. Each treatment group consists of 30 animals, this number is justified according to a schedule that involves the sacrifice of animals throughout the experiment to evaluate colonization of the bacteria in internal organs, where animals are understood as poultry.

A standardized vaccination schedule model was followed according to the following schedule:

TABLE 3

Schedule for vaccination schedules

| Schedule | Type of samples | Laboratory | (ELISA, PCR, Culture) | Day 0 | 7 | 14 | 21 | 28 |
|---|---|---|---|---|---|---|---|---|
| Date |  |  |  |  |  |  |  |  |
| Age of the bird |  |  |  | 1 day | 8 days | 15 days | 22 days | 29 days |
| Vaccine 1st dose |  |  |  | X |  |  |  |  |
| Challenge |  |  |  |  |  |  | X |  |
| Blood | Serum | LMS | ELISA | X | X | X | X | X |
| Organs | Liver, spleen, stool, drag swab | LBMG/LMS | PCR/ Microbiological culture | X | X | X | X | X |
| Other |  |  |  |  |  |  |  |  |

LMS: Microbiology and serology laboratory
LBMG: Laboratory of molecular biology and genomics At this point, SPF Hyline 1-day-old chickens are used, which are vaccinated according to the aforementioned scheme. After vaccination, the birds are monitored for the observation of clinical signs. Each experimental group is kept in separate cages. On day 21, the birds are challenged intramuscularly with $10^{10}$ copies/mL of AvA-I serotype IV, which is equivalent to $10^5$ $IDCE_{50}$ (mean infective dose in chicken embryo). One of the groups are challenged with both AvA-I (intramuscularly) and with a wild strain of *Salmonella enteritidis* (orally, $10^7$ copies/mL). Samples are taken at regular intervals, according to the established schedule that will include feces, cloacal swabs, liver and spleen for the detection and quantification of RAvA-SE, wild SE and AvA-I. Blood samples are also considered according to the schedule for the measurement of protective antibodies. At 7 days post-challenge, all birds are euthanized.

Determination of Excretion and Colonization of Attenuated *Salmonella enteritidis* in Chickens At this point, the animal tests allow determining that the attenuated *Salmonella enteritidis* strain (ASE) provides the characteristics under which it has been designed: avirulent, decreased colonization capacity, persistence and excretion, compared with a wild field strain.

The work schedule was designed specifying: treatment groups, route of administration, concentration of the bacteria to be used, type of sample to be evaluated and the days of sampling. Each treatment consists of 15 animals, this number includes the euthanasia of animals on the days indicated in the schedule, to evaluate colonization of the bacteria in internal organs. The 1-day-old birds separated by group according to treatment are inoculated with the ASE strain using a sterile 1 mL syringe. Birds are monitored daily for clinical signs, providing food and ad libitum water. The conditions of relative humidity and the appropriate light-dark cycles are maintained. The birds at the end of the experiment were euthanized by electric shock.

According to the design of the experiment, samples are sent to the laboratory for the respective microbiological, serological and molecular analysis.

Microbiological Assays for the Detection and Quantification of *Salmonella*.

They allow determining excretion and tissue colonization of the ASE bacterium throughout the experiment, according to the established sample shipment schedule.

Stool samples, rectal swabs, spleen and liver from the birds of the different groups evaluated are analyzed throughout the experiment according to the established sample shipment schedule. The procedure for isolation is carried out as indicated by the flow chart (FIG. 9).

The bacterial load in the samples was determined.

LIST OF FIGURES

FIG. 1: Allelic exchange method for the construction of 3934vacR.

FIG. 2: Integrative plasmid pKO

FIG. 3: Integrative plasmid pKO::waaL

FIG. 4: Waa region (rfa) of *Salmonella enteritidis* 3934vac

FIG. 5: Waa region (rfa) of *Salmonella enteritidis* 3934vacR

FIG. 6: pKOB::sb13 Plasmid

FIG. 7: pKOB::sb13 fiber Plasmid

FIG. 8: Phenotypic differentiation of *Salmonella* strains on Congo red agar plates (left) and semisolid agar (right).

FIG. 9: Flow chart for the detection and microbiological quantification of *Salmonella*. In addition, TSI: Triple sugar iron agar; LIA: Lysine iron agar.

FIG. 10: Western blot results of the protein of interest clyA-fiberFAdV-His.

FIG. 11: SDS-PAGE results of the protein of interest clyA-fiberFAdV-His, with positive controls A and B.

FIG. 12: Coomassie staining of the SDS-PAGE and Western Blot of the protein extracts obtained after growth in LB medium at 37° C. or 28° C. In addition, MW: molecular weight marker, wt: *Salmonella enteritidis* 3934, A: *Salmonella enteritidis* 3934Vac; A-fiber: *Salmonella enteritidis* 3934Vac with ClyA-fiberFAdV-His fusion on the chromosome, A-pfiber: *Salmonella enteritidis* 3934Vac expressing the ClyA-fiberFAdV-His fusion from plasmid. The specific bands obtained in the western blot have been indicated (A, B and C).

FIG. 13: Electrophoretic analysis of the PCR products reveals the presence of clones carrying the waaL deletion. For the selection of clones carrying the deletion, the bacterial chromosome was amplified using oligos external to the construct. In addition, M=molecular weight marker, wt=wild strain, c=colony. Expected sizes: Wt=2328 bp, ΔwaaL=1112 bp FIG. 14: Summary table of oligos used

PREFERRED EMBODIMENT OF THE INVENTION: EXAMPLES

The following examples that are provided herein serve to illustrate the nature of the present invention. These examples are included for illustrative purposes only and should not be interpreted as limitations of the invention claimed herein.

Example 1: Expression of the Fiber Antigen in the *Salmonella enteritidis* 3934 Vac Strain by Western Blot Protein Extract We plated 1 colony in 5 mL of LB culture medium for the ClyA fiber, which has the insertion in the chromosome. Incubate at 37° C. at 200 rpm overnight.

We centrifuged at 11 0000 rpm for 5 minutes and added the lysis buffer 1 (Tris HCL 10 Mm, EDTA 5 mM, NaCl 50 mM)+protease inhibitor 40 µL (3 g/mL)+50 µL of lysozyme (10 mg/mL), plus the SDS loading buffer (50 µL simple buffer 2x+50 µL urea 8M+5 µL B-mercaptoethanol in 50 µL sample) per sample and all was homogenized and heated at 100° C. for 5 minutes and then placed on ice 5 minutes and from there 20 µL was taken for loading. 0.1 Amps were used for each gel by 1:30.

Figure 10:
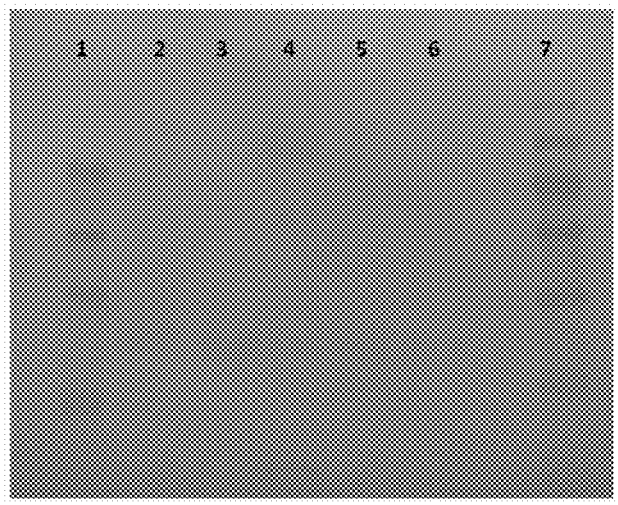

The band of the protein of interest clyA-fiberFAdV-His was observed in the results of the Western blot. Markers were used; on the left the ladder P7709V (175 KDa), on the right ab 116029 (245 KDa) (FIG. 10).

Figure 11:
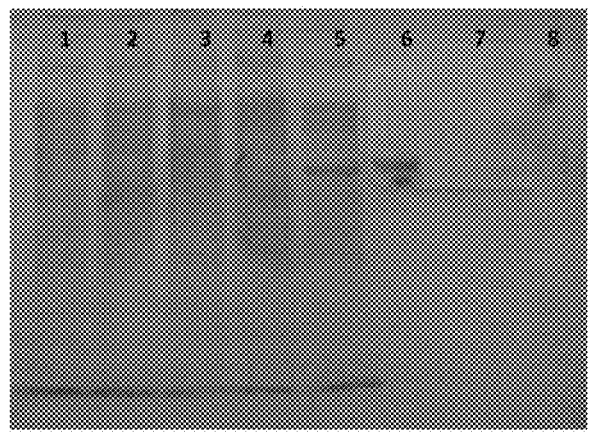
Figure 12:
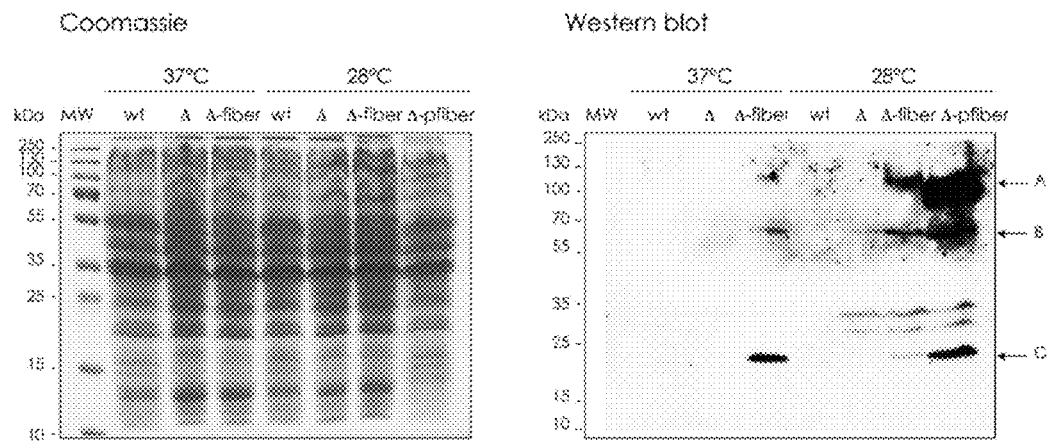

In addition, when two positive His+ controls are used, but the initials A and B are by weight, A is approximately 60 kDa and B is approximately 30 kDa. These results allow us concluding that the clyA-fiberFAdV-His fusion is expressed with a molecular weight of approx. of 85.4 kDa. (FIG. 11)

The Western blot was performed for the wild strain: *Salmonella enteritidis* 3934, Δ: *Salmonella enteritidis* 3934Vac; Δ-fiber: *Salmonella enteritidis* 3934Vac with ClyA-fiberFAdV-His fusion on the chromosome, Δ-pfiber: *Salmonella enteritidis* 3934Vac expressing the cly-ΔfiberFAdV-His fusion from plasmid.

Figure 13:
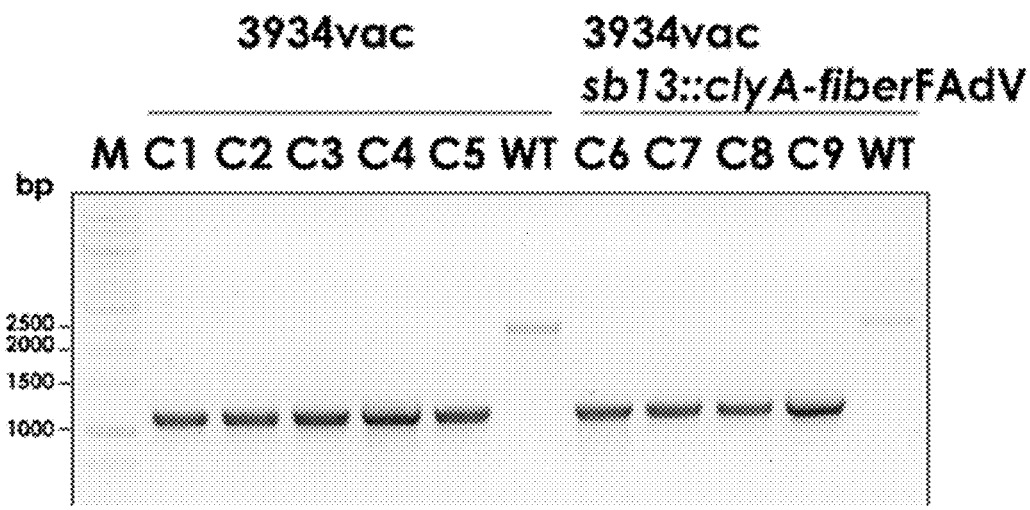

Electrophoretic analysis of the PCR products reveals the presence of clones carrying the waaL deletion (FIG. 13)

For the purposes of the present invention, the use of the *Salmonella enteritidis* 3934vac strain in experimental models suggested that it would work in murine and even avian model, In our trials, we have observed that when inoculated into birds, it does not work well because the infection develops anyway; in order to achieve immunity, a deletion was made in the waaL gene of *Salmonella enteritidis* 3934vac, with which immunity was achieved. Likewise, the challenge tests with the 3934vac sb13::clyA-fiberFAdV ΔwaaL strain demonstrated that it confers immunity against *Salmonella* and the avian type-I Adenovirus preventing the appearance of inclusion body hepatitis.

Deposit of Microorganisms

The strains of SG-9R sb:ClyA-FIBER 6His, 3934 vac-rough mutant and 3934 vac-Fiber rough mutant have been deposited in the Spanish Type Culture Collection (Paterna, Valencia, Spain), following the rules of the Budapest Treaty for the deposit of microorganisms for patent purposes on the following dates and they have been assigned the following deposit number:

| Material | Deposit date | Access Number |
| --- | --- | --- |
| SG-9Rsb:ClyA-FIBER 6His | Apr. 5, 2017 | CET 9331 |
| 3934 vac- rough mutant | Apr. 5, 2017 | CET 9332 |
| 3934 vac- Fiber rough mutant | Apr. 5, 2017 | CET 9333 |

The present invention is not limited to the scope of the microorganisms deposited in the patent, since they represent a specific illustration of an aspect of the invention. Any microorganism or plasmid that is functionally equivalent to those described in the invention are included within the invention.

The invention claimed is:

1. A mutant strain of *Salmonella enteritidis* 3934vac wherein it comprises a deletion of the waaL gene.

2. Method for generating a mutant strain of *Salmonella enteritidis* 3934vac, wherein it comprises:
   Construct an integrative vector, where for the construction of the integrative vector, two fragments flanking the waaL gene, one of 520 bp (oligonucleotides A and B) and the other of 504 bp (oligonucleotides C and D), respectively, are amplified by PCR, where the oligonucleotides A, B, C and D are the sequences SEQ ID NO:3, SEQ ID NO:4, SEQ ID NO:5, SEQ ID NO:6;
   Purify and clone the PCR products separately in pKOB vectors for amplification, to obtain the resulting pKOB::waaL vector for its amplification, then enzymatically digest, purify and bind in the pDESTINATION vector;
   Transform the resulting vector pDEST::*waaL* into *Escherichia coli* and verify by PCR, miniprep and digestion; once constructed, the pDEST::*waaL* plasmid is electroporated into the *Salmonella enteritidis* 3934vac and 3934vac sb13::clyA-fiberFAdV strains, where its integration is forced by growth at 42° C. and subsequent excision at 28° C.;
   Verify the deletion of the waaL gene by double homologous recombination by PCR with oligos external to the construction (waaL E and F), where oligos E and F are SEQ ID NO:9 and SEQ ID NO:10; and
   Adding said modified mutant strain of *Salmonella enteritidis* 3934vac to a composition to make a vaccine comprising said modified mutant strain of *Salmonella enteritidis* 3934vac with a deletion of the waaL gene.

3. A mutant strain of *Salmonella enteritidis* 3934vac wherein it comprises the complete sequence of the AvA-1 fiber gene and a deletion of the waaL gene.

4. Method for generating a mutant strain of *Salmonella enteritidis* 3934vac wherein it comprises:
   Have a strain of *Salmonella enteritidis* 3934vac;
   Insert a selection cassette by means of a first step of homologous recombination, wherein the cassette contains sequences complementary to the prophage ST64B in its flanking regions, in addition to the gene for resistance to antibiotic; where the bacterium is electroporated in the presence of the linear DNA carrying the selection cassette in the first step of homologous recombination;
   Select the transformant colonies in LB medium containing the antibiotic after the first step of homologous recombination;
   Confirm the presence of the cassette in the chromosome of *Salmonella enteritidis* 3934 by PCR with the oligos of sequences SEQ ID NO:23, SEQ ID NO:24 and SEQ ID NO:257;
   Insert a ClyA-fiberFAdV-His expression cassette by a second step of homologous recombination, where the expression cassette replaces the selection cassette, where the expression cassette comprises the sequence SEQ ID NO:21; and
   Select the strains of *Salmonella enteritidis* 3934vac sb13::clyA-fiberFAdV by verifying the product of the expression of the sequence SEQ ID NO:21 by Western Blot and SDS-PAGE.

5. Method according to claim 4, wherein it also comprises:
   Construct an integrative vector, where two fragments flanking the waaL gene, one of 520 bp gene (oligonucleotides A and B of sequences SEQ ID NO:3 and SEQ ID NO:4, respectively) and other of 504 bp (oligonucleotides C and D of sequences SEQ ID NO:5 and SEQ ID NO:6, respectively) are amplified by PCR for the construction of the integrative vector;
   Purify and clone the PCR products separately in pKOB vectors for amplification, to obtain the resulting vector pKOB::*DwaaLR*1 for its amplification, then enzymatically digest, purify and bind in the pDESTINATION vector;
   Transform the resulting vector pDEST::*waaL* in *Escherichia coli* and verify by PCR, miniprep and digestion; once constructed, the pDEST::*waaL* plasmid is electroporated in the *Salmonella enteritidis* 3934vac and 3934vac sb13::clyA-fiberFAdV strains, wherein its integration is forced by growth at 42° C. and subsequent excision at 28° C.; and Verify by PCR with oligos SEQ ID NO:9 and SEQ ID NO:10, external to the construction, the deletion of the *waaL* gene by double homologous recombination.

6. Recombinant avian vaccine of *Salmonella enteritidis* wherein it comprises a modified mutant strain of *Salmonella enteritidis* 3934vac with a sequence of the AvA-I fiber gene and a deletion of the waaL gene.

7. A mutant strain of *Salmonella enteritidis* 3934vac wherein it comprises an expression cassette SEQ ID NO:21 and the deletion of waaL that is verified by the presence of the sequence SEQ ID NO:8.

8. A mutant strain of *Salmonella enteritidis* 3934vac wherein it comprises a sequence SEQ ID NO:26 and SEQ ID NO:8.

* * * * *

SEQUENCE LISTING

```
<160> NUMBER OF SEQ ID NOS: 26

<210> SEQ ID NO 1
<211> LENGTH: 7999
<212> TYPE: DNA
<213> ORGANISM: Artificial Sequence
<220> FEATURE:
<223> OTHER INFORMATION: pKO
<220> FEATURE:
<221> NAME/KEY: misc_feature
<222> LOCATION: (1039)..(1039)
<223> OTHER INFORMATION: n is a, c, g, or t
<220> FEATURE:
<221> NAME/KEY: misc_feature
<222> LOCATION: (3427)..(3427)
<223> OTHER INFORMATION: n is a, c, g, or t
<220> FEATURE:
<221> NAME/KEY: misc_feature
<222> LOCATION: (3979)..(3980)
<223> OTHER INFORMATION: n is a, c, g, or t
<220> FEATURE:
<221> NAME/KEY: misc_feature
<222> LOCATION: (3983)..(3983)
<223> OTHER INFORMATION: n is a, c, g, or t
<220> FEATURE:
<221> NAME/KEY: misc_feature
<222> LOCATION: (5891)..(5892)
<223> OTHER INFORMATION: n is a, c, g, or t
```

```
<220> FEATURE:
<221> NAME/KEY: misc_feature
<222> LOCATION: (7966)..(7966)
<223> OTHER INFORMATION: n is a, c, g, or t

<400> SEQUENCE: 1
ccctttcgtc ttcgaataaa tacctgtgac ggaagatcac ttcgcagaat aaataaatcc      60
tggtgtccct gttgataccg ggaagccctg ggccaacttt tggcgaaaat gagacgttga     120
tcggcacgta agaggttcca actttcacca taatgaaata agatcactac cgggcgtatt     180
ttttgagtta tcgagatttt caggagctaa ggaagctaaa atggagaaaa aaatcactgg     240
atataccacc gttgatatat cccaatggca tcgtaaagaa cattttgagg catttcagtc     300
agttgctcaa tgtacctata accagaccgt tcagctggat attacggcct ttttaaagac     360
cgtaaagaaa aataagcaca agttttatcc ggcctttatt cacattcttg cccgcctgat     420
gaatgctcat ccggaattcc gtatggcaat gaaagacggt gagctggtga tatgggatag     480
tgttcaccct tgttacaccg ttttccatga gcaaactgaa acgttttcat cgctctggag     540
tgaataccac gacgatttcc ggcagtttct acacatatat tcgcaagatg tggcgtgtta     600
cggtgaaaac ctggcctatt tccctaaagg gtttattgag aatatgtttt tcgtctcagc     660
caatccctgg gtgagtttca ccagttttga tttaaacgtg gccaatatgg acaacttctt     720
cgcccccgtt ttcaccatgg gcaaatatta tacgcaaggc gacaaggtgc tgatgccgct     780
ggcgattcag gttcatcatg ccgtttgtga tggcttccat gtcggcagaa tgcttaatga     840
attacaacag tactgcgatg agtggcaggg cggggcgtaa ttttttttaag gcagttattg     900 gtgcccttaa acgcctggtg ctacgcctga ataagtgata taagcggat gaatggcaga     960 aattcgaaag caaattcgac ccggtcgtcg gttcagggca gggtcgttaa atagccgctt    1020
atgtctattg ctggttttant cggtaccccc tttagcatat tatgttgcca actgtcggaa    1080
cgagacttct ctaaaccttc ccggcttcat catgctctct taacactgct acatcaaccc    1140
cttgaatcct caattcacct cctcgaaaac atttcccatc aatcatattc tggtatatct    1200
tatcttctgg cagtgacagc gtcacttcgt aatcattatg attgatgata atcaaatact    1260
tccattcatc agtctctctt tgttgcacct ctacattttc agctacttca agaatgggat    1320
taatatgatg tttagcgaaa acctgttcta aaagcctgcc taaataatta ctatctggat    1380
aagtaccgac gtaaatcccc tctcctttac cgtagcagtt acgtgtaacc gccggaagtc    1440
ctgcatacca atccccctta aatgtcgcta gaggttctgc cccttctaat cggattatgt    1500
ccgcccacgt cgtacaatca tattccccat cgttactata tattttgttt acctttgttt    1560
ctgggtatgg tacaaattcc tcaacaaaaa tccccaaaat atctcgcaga ggaccaggat    1620
atccgcctag atgtacacgg tcattttcat ctacaatgcc actgaagaaa ctgacaatca    1680
aagtgccacc gttagcaaca aattgccgta agttttcatc ttctccctct ttaaccatat    1740
ataacattgg agcaataact actttgtatt ttgttagatc atcagatggc cttacaaaat    1800
cgacagcaat attacgttta taattcccc tataataagc ttcaactata ggaatatatc    1860
ttagtttatt atgtggtttg gaacttagtt cgacagccca ccagtttccc caatcaaaaa    1920
tgatcgcgac ctctgccttg attctagatc cgaccaaaca atctaacttt ttcagctctt    1980
gccctaactg tgtaacttcc ctataaattc tattattctc gttcaaaaag tggggcacca    2040
ttgcaccgtg gaatttttca gctcctgctc tactttgacg ccactggaaa aacataaatac    2100 catctgcacc acgggcaata gttgcataac tccatagacg cattcaccct ggcggttttg    2160
```

```
gaacattaat atcgcgccag ttaacatgtg aggttacctg ctccatcaaa ataaacggtt    2220 gacctttttct taaactacgc ataaggtcat tcatcatggc gtgctgaatt ggcaagccct   2280
ctctgggatc aggatatgag tcccatgtca caatatctac atgctgagcc cattgaaaat   2340
agtttaacgg tttgaatgaa cccatgaaat tagttgatac tggaatatct ggtgttacct   2400
cacgtaaaat ttccttttct gttaaaaaca acttgagaat tgagtcattc ataaaacggt   2460
agtaatcaag ttcttgggat ggattaataa aagttggtgc ctttctaggg ggattaattt   2520
catcccaatg attgtatcgc tgtccccaaa agtttgtacc ccaacgttca tttaattcat   2580
cgattgtttt atatctttcc tttagccact ttctaaacgc gacagcacaa ttctcacaaa   2640
aacacttgga aacgtgacat gcatactcat tattaacatg ccacattttg agtgccggat   2700 gattttata ccgttctgct atagccctca caagtctctt tatgtgcgta attaattgag    2760
gatgattagg acaataatgt tgtctactgc caaacgagag aatgacaccg ctttcatcga   2820
tcggcaaaga atctggatac ttttttacaa accaagctgg agtagttgca gtcgccgtcc   2880
ccaagttaat ataaacaccg tggtcatata gtatatctat aaccttgtct agccattcaa   2940
agtcgaacac tccatcagac ggttcgatct tgctccaact gaaaatccct aaagatacta   3000 aattcaccccc cgcttttttgc atcaacttag catcttcata ccaaatttcc tctggccatt  3060
gctctgggtt ataatctcct ccgtaacaaa ttgaggataa cacattcata attattcccc   3120
ctagctaatt ttcgtttaat tataaattaa gttaaaattt aggtacctac gtaggatcga   3180
tccgatcctt aattatatta tagtcccaat ataatcattt atcaactctt ttacacttaa   3240
atttcctaat atttgtaaat attttttttga ataaaaaaat ctagctaatg ttacgttaca  3300
cattaactag acagatctat cgatgcatgc catggtaccc gggagctcga attctagaag   3360
cttctgcaga cgcgtcgacg tcatatggat cctctagagc ggccgcgatc ctctagagtc   3420
gaccggngaa tggcgaatgg gacgcgccct gtagcggcgc attaagcgcg gcgggtgtgg   3480
tggttacgcg cagcgtgacc gctacacttg ccagcgccct agcgcccgct cctttcgctt   3540
tcttcccttc ctttctcgcc acgttcgccg gctttccccg tcaagctcta atcgggggc    3600 tccctttagg gttccgattt agtgctttac ggcacctcga ccccaaaaaa cttgattagg   3660
gtgatggttc acgtagtggg ccatcgccct gatagacggt ttttcgccct tgacgttgg    3720 agtccacgtt ctttaatagt ggactcttgt tccaaactgg aacaacactc aaccctatct   3780
cggtctattc ttttgattta aagggatttt gccgatttc ggcctattgg ttaaaaaatg    3840
agctgattta acaaaaattt aacgcgaatt ttaacaaaat attaacgctt acaatttagg   3900
tggcactttt cggggaaatg tgcgcggaac ccctatttgt ttatttttct aaatacattc   3960
aaatatgtat ccgctcatnn cangatcctt tttaacccat cacatatacc tgccgttcac   4020
tattatttag tgaaatgaga tattatgata ttttctgaat tgtgattaaa aaggcaactt   4080
tatgcccatg caacagaaac tataaaaaat acagagaatg aaaagaaaca gatagatttt   4140
ttagttcttt aggcccgtag tctgcaaatc cttttatgat tttctatcaa acaaaagagg   4200
aaaatagacc agttgcaatc caaacgagag tctaatagaa tgaggtcgaa agtaaatcg    4260 cgcgggtttt ttactgataa agcaggcaag acctaaaatg tgtaaagggc aaagtgtata   4320
ctttggcgtc accccttaca tattttaggt cttttttttat tgtgcgtaac taacttgcca  4380
tcttcaaaca ggagggctgg aagaagcaga ccgctaacac agtacataaa aaaggagaca   4440
tgaacgatga acatcaaaaa gtttgcaaaa caagcaacag tattaacctt tactaccgca   4500
ctgctggcag gaggcgcaac tcaagcgttt gcgaaagaaa cgaaccaaaa gccatataag   4560
```

```
gaaacatacg gcatttccca tattacacgc catgatatgc tgcaaatccc tgaacagcaa    4620
aaaaatgaaa aatatcaagt tcctgaattc gattcgtcca caattaaaaa tatctcttct    4680
gcaaaaggcc tggacgtttg ggacagctgg ccattacaaa acgctgacgg cactgtcgca    4740
aactatcacg gctaccacat cgtctttgca ttagccggag atcctaaaaa tgcggatgac    4800
acatcgattt acatgttcta tcaaaaagtc ggcgaaactt ctattgacag ctggaaaaac    4860
gctggccgcg tctttaaaga cagcgacaaa ttcgatgcaa atgattctat cctaaaagac    4920
caaacacaag aatggtcagg ttcagccaca tttacatctg acggaaaaat ccgtttattc    4980
tacactgatt tctccggtaa acattacggc aaacaaacac tgacaactgc acaagttaac    5040
gtatcagcat cagacagctc tttgaacatc aacggtgtag aggattataa atcaatcttt    5100
gacggtgacg gaaaaacgta tcaaaatgta cagcagttca tcgatgaagg caactacagc    5160
tcaggcgaca accatacgct gagagatcct cactacgtag aagataaagg ccacaaatac    5220
ttagtatttg aagcaaacac tggaactgaa gatggctacc aaggcgaaga atctttatt t   5280 aacaaagcat actatggcaa aagcacatca ttcttccgtc aagaaagtca aaaacttctg    5340
caaagcgata aaaacgcac ggctgagtta gcaaacggcg ctctcggtat gattgagcta    5400
aacgatgatt acacactgaa aaaagtgatg aaaccgctga ttgcatctaa cacagtaaca    5460
gatgaaattg aacgcgcgaa cgtctttaaa atgaacggca aatggtacct gttcactgac    5520
tcccgcggat caaaaatgac gattgacggc attacgtcta acgatattta catgcttggt    5580
tatgtttcta attctttaac tggcccatac aagccgctga acaaaactgg ccttgtgtta    5640
aaaatggatc ttgatcctaa cgatgtaacc tttacttact cacacttcgc tgtacctcaa    5700
gcgaaaggaa acaatgtcgt gattacaagc tatatgacaa acagaggatt ctacgcagac    5760
aaacaatcaa cgtttgcgcc aagcttcctg ctgaacatca aaggcaagaa acatctgtt    5820 gtcaaagaca gcatccttga acaaggacaa ttaacagtta acaataaaa acgcaaaaga    5880 aaatgccgat nnccggttta ttgactaccg gaagcagtgt gaccgtgtgc ttctcaaatg    5940
cctcaggctg tctatgtgtg actgttgagc tgtaacaagt tgtctcaggt gttcaatttc    6000
atgttctagt tgctttgttt tactggtttc acctgttcta ttaggtgtta catgctgttc    6060
atctgttaca ttgtcgatct gttcatggtg aacagcttta aatgcaccaa aaactcgtaa    6120
aagctctgat gtatctatct tttttacacc gttttcatct gtgcatatgg acagttttcc    6180
ctttgatatc taacggtgaa cagttgttct acttttgttt gttagtcttg atgcttcact    6240
gatagataca agagccataa gaacctcaga tccttccgta tttagccagt atgttctcta    6300
gtgtggttcg ttgttttgc gtgagccatg agaacgaacc attgagatca tgcttacttt    6360
gcatgtcact caaaaatttt gcctcaaaac tggtgagctg aattttttgca gttaaagcat    6420 cgtgtagtgt ttttcttagt ccgttacgta ggtaggaatc tgatgtaatg gttgttggta    6480
ttttgtcacc attcattttt atctggttgt tctcaagttc ggttacgaga tccatttgtc    6540
tatctagttc aacttggaaa atcaacgtat cagtcgggcg gcctcgctta tcaaccacca    6600
atttcatatt gctgtaagtg tttaaatctt tacttattgg tttcaaaacc cattggttaa    6660 gcctttttaaa ctcatggtag ttattttcaa gcattaacat gaacttaaat tcatcaaggc    6720
taatctctat atttgccttg tgagttttct tttgtgttag ttctttaat aaccactcat     6780 aaatcctcat agagtatttg ttttcaaaag acttaacatg ttccagatta tattttatga    6840
atttttttaa ctggaaaaga taaggcaata tctcttcact aaaaactaat tctaattttt    6900
```

-continued

```
cgcttgagaa cttggcatag tttgtccact ggaaaatctc aaagccttta accaaaggat      6960
tcctgatttc cacagttctc gtcatcagct ctctggttgc tttagctaat acaccataag      7020
cattttccct actgatgttc atcatctgag cgtattggtt ataagtgaac gataccgtcc      7080
gttctttcct tgtagggttt tcaatcgtgg ggttgagtag tgccacacag cataaaatta      7140
gcttggtttc atgctccgtt aagtcatagc gactaatcgc tagttcattt gctttgaaaa      7200
caactaattc agacatacat ctcaattggt ctaggtgatt ttaatcacta taccaattga      7260
gatgggctag tcaatgataa ttactagtcc ttttcctttg agttgtgggt atctgtaaat      7320
tctgctagac ctttgctgga aaacttgtaa attctgctag accctctgta aattccgcta      7380
gacctttgtg tgttttttt gtttatattc aagtggttat aatttataga ataaagaaag      7440
aataaaaaaa gataaaaaga atagatccca gccctgtgta taactcacta ctttagtcag      7500
ttccgcagta ttacaaaagg atgtcgcaaa cgctgtttgc tcctctacaa aacagacctt      7560
aaaaccctaa aggcttaagt agcaccctcg caagctcggg caaatcgctg aatattcctt      7620
ttgtctccga ccatcaggca cctgagtcgc tgtcttttc gtgacattca gttcgctgcg      7680
ctcacggctc tggcagtgaa tgggggtaaa tggcactaca ggcgccttt atggattcat      7740 gcaaggaaac tacccataat acaagaaaag cccgtcacgg gcttctcagg gcgttttatg      7800
gcgggtctgc tatgtggtgc tatctgactt tttgctgttc agcagttcct gccctctgat      7860
tttccagtct gaccacttcg gattatcccg tgacaggtca ttcagactgg ctaatgcacc      7920
cagtaaggca gcggtatcat caacaggctt accgtcttta ctgtcnggat cgacgctctc      7980
ccttatgcga ctcctgcat                                                   7999

<210> SEQ ID NO 2
<211> LENGTH: 8926
<212> TYPE: DNA
<213> ORGANISM: Artificial Sequence
<220> FEATURE:
<223> OTHER INFORMATION: pKO::waaL
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (2108)..(2109)
<223> OTHER INFORMATION: n is a, c, g, or t
<220> FEATURE:
<221> NAME/KEY: misc_feature
<222> LOCATION: (4017)..(4017)
<223> OTHER INFORMATION: n is a, c, g, or t
<220> FEATURE:
<221> NAME/KEY: misc_feature
<222> LOCATION: (4020)..(4021)
<223> OTHER INFORMATION: n is a, c, g, or t
<220> FEATURE:
<221> NAME/KEY: misc_feature
<222> LOCATION: (4573)..(4573)
<223> OTHER INFORMATION: n is a, c, g, or t
<220> FEATURE:
<221> NAME/KEY: misc_feature
<222> LOCATION: (7888)..(7888)
<223> OTHER INFORMATION: n is a, c, g, or t

<400> SEQUENCE: 2
atgcaggagt cgcataaggg agagcgtcga tccngacagt aagacgggta agcctgttga       60
tgataccgct gccttactgg gtgcattagc cagtctgaat gacctgtcac gggataatcc      120
gaagtggtca gactggaaaa tcagagggca ggaactgctg aacagcaaaa agtcagatag      180
caccacatag cagacccgcc ataaaacgcc ctgagaagcc cgtgacgggc ttttcttgta      240
```

```
ttatgggtag tttccttgca tgaatccata aaaggcgcct gtagtgccat ttaccccat      300 tcactgccag agccgtgagc gcagcgaact gaatgtcacg aaaaagacag cgactcaggt     360
gcctgatggt cggagacaaa aggaatattc agcgatttgc ccgagcttgc gagggtgcta    420
cttaagcctt tagggtttta aggtctgttt tgtagaggag caaacagcgt ttgcgacatc    480
cttttgtaat actgcggaac tgactaaagt agtgagttat acacagggct gggatctatt   540 cttttatct tttttattc tttctttatt ctataaatta taaccacttg aatataaaca      600 aaaaaacac acaaaggtct agcggaattt acagagggtc tagcagaatt tacaagtttt     660
ccagcaaagg tctagcagaa tttacagata cccacaactc aaaggaaaag gactagtaat    720
tatcattgac tagcccatct caattggtat agtgattaaa atcacctaga ccaattgaga    780
tgtatgtctg aattagttgt tttcaaagca aatgaactag cgattagtcg ctatgactta    840
acggagcatg aaaccaagct aattttatgc tgtgtggcac tactcaaccc cacgattgaa   900
aaccctacaa ggaagaacg gacggtatcg ttcacttata accaatacgc tcagatgatg     960
aacatcagta gggaaaatgc ttatggtgta ttagctaaag caaccagaga gctgatgacg   1020
agaactgtgg aaatcaggaa tcctttggtt aaaggctttg agattttcca gtggacaaac   1080
tatgccaagt tctcaagcga aaaattagaa ttagttttta gtgaagagat attgccttat    1140
cttttccagt taaaaaatt cataaaatat aatctggaac atgttaagtc ttttgaaaac    1200
aaatactcta tgaggattta tgagtggtta ttaaaagaac taacacaaaa gaaaactcac   1260
aaggcaaata tagagattag ccttgatgaa tttaagttca tgttaatgct tgaaaataac   1320
taccatgagt ttaaaaggct taaccaatgg gttttgaaac aataagtaa agatttaaac     1380 acttacagca atatgaaatt ggtggttgat aagcgaggcc gcccgactga tacgttgatt   1440
ttccaagttg aactagatag acaaatggat ctcgtaaccg aacttgagaa caaccagata   1500
aaaatgaatg gtgacaaaat accaacaacc attacatcag attcctacct acgtaacgga   1560
ctaagaaaaa cactacacga tgctttaact gcaaaaattc agctcaccag ttttgaggca   1620 aaattttga gtgacatgca aagtaagcat gatctcaatg gttcgttctc atggctcacg    1680
caaaaacaac gaaccacact agagaacata ctggctaaat acggaaggat ctgaggttct   1740
tatggctctt gtatctatca gtgaagcatc aagactaaca acaaaagta gaacaactgt    1800 tcaccgttag atatcaaagg gaaaactgtc catatgcaca gatgaaaacg gtgtaaaaaa   1860
gatagataca tcagagcttt tacgagtttt tggtgcattt aaagctgttc accatgaaca   1920
gatcgacaat gtaacagatg aacagcatgt aacacctaat agaacaggtg aaaccagtaa   1980
aacaaagcaa ctagaacatg aaattgaaca cctgagacaa cttgttacag ctcaacagtc   2040
acacatagac agcctgaggc atttgagaag cacacggtca cactgcttcc ggtagtcaat   2100
aaaccggnna tcggcatttt cttttgcgtt tttatttgtt aactgttaat tgtccttgtt   2160
caaggatgct gtctttgaca acagatgttt tcttgccttt gatgttcagc aggaagcttg   2220
gcgcaaacgt tgattgtttg tctgcgtaga atcctctgtt tgtcatatag cttgtaatca   2280
cgacattgtt tcctttcgct tgaggtacag cgaagtgtga gtaagtaaag gttacatcgt   2340
taggatcaag atccattttt aacacaaggc cagttttgtt cagcggcttg tatgggccag   2400
ttaaagaatt agaaacataa ccaagcatgt aaatatcgtt agacgtaatg ccgtcaatcg   2460 tcattttga tccgcgggag tcagtgaaca ggtaccattt gccgttcatt ttaaagacgt   2520
tcgcgcgttc aatttcatct gttactgtgt tagatgcaat cagcggtttc atcacttttt   2580
```

```
tcagtgtgta atcatcgttt agctcaatca taccgagagc gccgtttgct aactcagccg      2640 tgcgttttt  atcgctttgc agaagttttt gactttcttg acggaagaat gatgtgcttt      2700
tgccatagta tgctttgtta ataaagatt  cttcgccttg gtagccatct tcagttccag      2760
tgtttgcttc aaatactaag tatttgtggc ctttatcttc tacgtagtga ggatctctca      2820
gcgtatggtt gtcgcctgag ctgtagttgc cttcatcgat gaactgctgt acattttgat      2880 acgttttcc  gtcaccgtca aagattgatt tataatcctc tacaccgttg atgttcaaag      2940
agctgtctga tgctgatacg ttaacttgtg cagttgtcag tgtttgtttg ccgtaatgtt      3000
taccggagaa atcagtgtag aataaacgga ttttccgtc  agatgtaaat gtggctgaac      3060
ctgaccattc ttgtgtttgg tcttttagga tagaatcatt tgcatcgaat tgtcgctgt       3120 cttaaagac  gcggccagcg ttttccagc  tgtcaataga agtttcgccg acttttgat       3180 agaacatgta aatcgatgtg tcatccgcat ttttaggatc tccggctaat gcaaagacga      3240
tgtggtagcc gtgatagttt gcgacagtgc cgtcagcgtt ttgtaatggc cagctgtccc      3300
aaacgtccag gccttttgca gaagagatat ttttaattgt ggacgaatcg aattcaggaa      3360
cttgatattt ttcattttt  tgctgttcag ggatttgcag catatcatgg cgtgtaatat      3420
gggaaatgcc gtatgtttcc ttatatggct tttggttcgt ttctttcgca aacgcttgag      3480
ttgcgcctcc tgccagcagt gcggtagtaa aggttaatac tgttgcttgt tttgcaaact      3540
ttttgatgtt catcgttcat gtctcctttt ttatgtactg tgttagcggt ctgcttcttc      3600
cagccctcct gtttgaagat ggcaagttag ttacgcacaa taaaaaaga  cctaaaatat      3660 gtaaggggtg acgccaaagt atacactttg ccctttacac attttaggtc ttgcctgctt      3720
tatcagtaac aaacccgcgc gatttacttt tcgacctcat tctattagac tctcgtttgg      3780
attgcaactg gtctattttc ctcttttgtt tgatagaaaa tcataaaagg atttgcagac      3840
tacgggccta agaactaaa  aaatctatct gtttcttttc attctctgta tttttatag      3900 tttctgttgc atgggcataa agttgccttt ttaatcacaa ttcagaaaat atcataaat      3960 ctcatttcac taaataatag tgaacggcag gtatatgtga tgggttaaaa aggatcntgn      4020
natgagcgga tacatatttg aatgtattta gaaaataaa  caaataggg  ttccgcgcac      4080 atttccccga aaagtgccac ctaaattgta agcgttaata ttttgttaaa attcgcgtta      4140 aattttgtt  aaatcagctc attttttaac caataggccg aaatcggcaa atcccttat      4200 aaatcaaaag aatagaccga datagggttg agtgttgttc cagtttggaa caagagtcca      4260
ctattaaaga acgtggactc caacgtcaaa gggcgaaaaa ccgtctatca gggcgatggc      4320
ccactacgtg aaccatcacc ctaatcaagt ttttggggt  cgaggtgccg taaagcacta      4380
aatcggaacc ctaaagggag cccccgattt agagcttgac ggggaaagcc ggcgaacgtg      4440
gcgagaaagg aagggaagaa agcgaaagga gcgggcgcta gggcgctggc aagtgtagcg      4500
gtcacgctgc gcgtaaccac cacacccgcc gcgcttaatg cgccgctaca gggcgcgtcc      4560
cattcgccat tcnccggtcg actctagagg atcgcggccg cgcgattatg ccatcgcaaa      4620 acatttctg  cattgccagc aggcggtcag cgatccatat gcggtattt  tacatgccac      4680 gacccgcgat gataaacact ggccggaagc aaactggcgc gagcttatcg gtatggtggg      4740
caacaccgga ttacggataa aacttccctg gggcgcgcct catgaggagg cccgggctaa      4800
acgactggcc gaaggctttg actatgtgga tgtgttaccg cgcatgagcc tggaggaggt      4860
cgccagagtg ctggctggcg caaaattgt  cgtatcggtt gataccggcc tgagccatct      4920
caccgccgcg ctcgacagac cgaatattac gctatatggc ccaacggacc ctgggttaat      4980
```

```
tggaggttat gggaagaacc aaatggcatg ctgctcacca gaaaaaaacc tggcgaattt    5040
agatgccaca agcgtatttg gaaagattca ttaaagagac actgtctcat cccaaaccta    5100
ttgtggactc gaggcgctga tacttattac ggtatcagcg cgttttccat cgtccggact    5160
caatcactta tcaaaccagc ttttcatctg ttcctcgaaa cgctgagcta cattttccca    5220
actgtatttt gaaaacacca gggattttgc ttttcggca atctggtggc gttccttatc     5280
agcaagcgca cggttaatat cattaattat actgtcgctc gacataggtt ctgcgaggtg    5340
atagcccgtt atgccatcta acacaaattc gctaatcccc ccttttttgc tggcaagaac    5400
cgcttttcct gctgccatcg cttctacagc caccatgcaa aatgcttctt caacctgaga    5460
tggcacaata accagatcgg ctatatgata aagttatgc atctggtcag gagattgccc     5520
cccagccata atacaatcag ttccaatctc ttttgcggcg tccagtactt tcttttgata    5580
ctctgctttt tcacccttgc ggcttagatc ttctgtctag ttaatgtgta acgtaacatt    5640
agctagattt ttttattcaa aaaatatttt acaaatatta ggaaatttaa gtgtaaaaga    5700
gttgataaat gattatattg ggactataat ataattaagg atcggatcga tcctacgtag    5760
gtacctaaat tttaacttaa tttataatta acgaaaatt agctagggg aataattatg      5820 aatgtgttat cctcaatttg ttacggagga gattataacc cagagcaatg gccagaggaa    5880
atttggtatg aagatgctaa gttgatgcaa aaagcgggggg tgaatttagt atctttaggg   5940
attttcagtt ggagcaagat cgaaccgtct gatggagtgt tcgactttga atggctagac    6000
aaggttatag atatactata tgaccacggt gtttatatta acttggggac ggcgactgca    6060
actactccag cttggtttgt aaaaagtat ccagattctt tgccgatcga tgaaagcggt     6120
gtcattctct cgtttggcag tagacaacat tattgtccta atcatcctca attaattacg    6180
cacataaaga gacttgtgag ggctatagca gaacggtata aaaatcatcc ggcactcaaa    6240
atgtggcatg ttaataatga gtatgcatgt cacgtttcca agtgtttttg tgagaattgt    6300
gctgtcgcgt ttagaaagtg gctaaaggaa agatataaaa caatcgatga attaaatgaa    6360
cgttggggta caaacttttg gggacagcga tacaatcatt gggatgaaat taatccccct    6420
agaaaggcac caacttttat taatccatcc caagaacttg attactaccg ttttatgaat    6480
gactcaattc tcaagttgtt tttaacagaa aaggaaattt tacgtgaggt aacaccagat    6540
attccagtat caactaattt catgggttca ttcaaaccgt taaactattt tcaatgggct    6600
cagcatgtag atattgtgac atgggactca tatcctgatc ccagagaggg cttgccaatt    6660
cagcacgcca tgatgaatga ccttatgcgt agtttaagaa aaggtcaacc gtttatttg     6720 atggagcagg taacctcaca tgttaactgg cgcgatatta atgttccaaa accgccaggt    6780
gtaatgcgtc tatggagtta tgcaactatt gcccgtggtg cagatggtat tatgttttc     6840 cagtggcgtc aaagtagagc aggagctgaa aaattccacg gtgcaatggt gccccacttt    6900
ttgaacgaga ataatagaat ttataggaa gttacacagt tagggcaaga gctgaaaaag     6960
ttagattgtt tggtcggatc tagaatcaag gcagaggtcg cgatcatttt tgattgggaa    7020
aactggtggg ctgtcgaact aagttccaaa ccacataata aactaagata tattcctata    7080
gttgaagctt attataggga attatataaa cgtaatattg ctgtcgattt tgtaaggcca    7140
tctgatgatc taacaaaata caaagtagtt attgctccaa tgttatatat ggttaaagag    7200
ggagaagatg aaaacttacg gcaatttgtt gctaacggtg gcactttgat tgtcagtttc    7260
ttcagtggca ttgtagatga aaatgaccgt gtacatctag gcggatatcc tggtcctctg    7320
```

```
cgagatatttt tggggatttt tgttgaggaa tttgtaccat acccagaaac aaaggtaaac    7380
aaaatatata gtaacgatgg ggaatatgat tgtacgacgt gggcggacat aatccgatta    7440 gaagggcag  aacctctagc gacatttaag ggggattggt atgcaggact tccggcggtt    7500
acacgtaact gctacggtaa aggagagggg atttacgtcg gtacttatcc agatagtaat    7560
tatttaggca ggcttttaga acaggttttc gctaaacatc atattaatcc cattcttgaa    7620
gtagctgaaa atgtagaggt gcaacaaaga gagactgatg aatggaagta tttgattatc    7680
atcaatcata atgattacga agtgacgctg tcactgccag aagataagat ataccagaat    7740
atgattgatg ggaaatgttt tcgaggaggt gaattgagga ttcaagggt  tgatgtagca    7800 gtgttaagag agcatgatga agccgggaag gtttagagaa gtctcgttcc gacagttggc    7860
aacataatat gctaaagggg gtaccganta aaccagcaat agacataagc ggctatttaa    7920
cgaccctgcc ctgaaccgac gaccgggtcg aatttgcttt cgaatttctg ccattcatcc    7980
gcttattatc acttattcag gcgtagcacc aggcgtttaa gggcaccaat aactgcctta    8040
aaaaaattac gccccgccct gccactcatc gcagtactgt tgtaattcat taagcattct    8100
gccgacatgg aagccatcac aaacggcatg atgaacctga atcgccagcg gcatcagcac    8160
cttgtcgcct tgcgtataat atttgcccat ggtgaaaacg ggggcgaaga agttgtccat    8220
attggccacg tttaaatcaa aactggtgaa actcacccag ggattggctg agacgaaaaa    8280
catattctca ataaaccctt tagggaaata ggccaggttt tcaccgtaac acgccacatc    8340
ttgcgaatat atgtgtagaa actgccggaa atcgtcgtgg tattcactcc agagcgatga    8400
aaacgtttca gtttgctcat ggaaaacggt gtaacaaggg tgaacactat cccatatcac    8460
cagctcaccg tctttcattg ccatacggaa ttccggatga gcattcatca ggcgggcaag    8520
aatgtgaata aaggccggat aaaacttgtg cttatttttc tttacggtct ttaaaaaggc    8580
cgtaatatcc agctgaacgg tctggttata ggtacattga gcaactgact gaaatgcctc    8640
aaaatgttct ttacgatgcc attgggatat atcaacggtg gtatatccag tgatttttt    8700 ctccatttta gcttccttag ctcctgaaaa tctcgataac tcaaaaaata cgcccggtag    8760
tgatcttatt tcattatggt gaaagttgga acctcttacg tgccgatcaa cgtctcattt    8820
tcgccaaaag ttggcccagg gcttcccggt atcaacaggg acaccaggat ttatttattc    8880
tgcgaagtga tcttccgtca caggtattta ttcgaagacg aaaggg                   8926

<210> SEQ ID NO 3
<211> LENGTH: 26
<212> TYPE: DNA
<213> ORGANISM: Artificial Sequence
<220> FEATURE:
<223> OTHER INFORMATION: oligo A

<400> SEQUENCE: 3
gcggccgcgc gattatgcca tcgcaa                                          26

<210> SEQ ID NO 4
<211> LENGTH: 25
<212> TYPE: DNA
<213> ORGANISM: Artificial Sequence
<220> FEATURE:
<223> OTHER INFORMATION: oligo B

<400> SEQUENCE: 4
ctcgagtcca caataggttt gggat                                           25
```

-continued

```
<210> SEQ ID NO 5
<211> LENGTH: 25
<212> TYPE: DNA
<213> ORGANISM: Artificial Sequence
<220> FEATURE:
<223> OTHER INFORMATION: oligo C

<400> SEQUENCE: 5
ctcgaggcgc tgatacttat tacgg                                          25

<210> SEQ ID NO 6
<211> LENGTH: 24
<212> TYPE: DNA
<213> ORGANISM: Artificial Sequence
<220> FEATURE:
<223> OTHER INFORMATION: oligo C

<400> SEQUENCE: 6
agatctaagc cgcaagggtg aaaa                                           24

<210> SEQ ID NO 7
<211> LENGTH: 2328
<212> TYPE: DNA
<213> ORGANISM: Artificial Sequence
<220> FEATURE:
<223> OTHER INFORMATION: 3934vac

<400> SEQUENCE: 7
tgggatacga taaaccgcag tcgcagggcg attatgccat cgcaaaacat tttctgcatt     60
gccagcaggc ggtcagcgat ccatatgcgg tattttttaca tgccacgacc cgcgatgata   120
aacactggcc ggaagcaaac tggcgcgagc ttatcggtat ggtgggcaac accggattac   180
ggataaaact tccctggggc gcgcctcatg aggaggcccg ggctaaacga ctggccgaag   240
gctttgacta tgtggatgtg ttaccgcgca tgagcctgga ggaggtcgcc agagtgctgg   300
ctggcgcaaa atttgtcgta tcggttgata ccggcctgag ccatctcacc gccgcgctcg   360
acagaccgaa tattacgcta tatggcccaa cggaccctgg gttaattgga ggttatggga   420
agaaccaaat ggcatgctgc tcaccagaaa aaaacctggc gaatttagat gccacaagcg   480
tatttggaaa gattcattaa agagacactg tctcatccca aacctattgt ggagaaaaga   540
tgctaaccac atcattaacg ttaaataaag agaaatggaa accgatctgg aataaagcgc   600 tggttttttct ttttgttgcc acgtattttc tggatggtat tacgcgttat aaacatttga   660
taatcatact tatggttatc accgcgattt atcaggtctc acgctcaccg aaaagtttcc   720
cccctctttt caaaaatagc gtattttata gcgtagcagt attatcatta atccttgttt   780
attccatact catatcgcca gatatgaaag aaagcttcaa ggaatttgaa atacggtac   840 tggagggttt cttattatat actttattaa ttcccgtact attaaaagat gaaacaaaag   900
aaacggttgc gaaaatagta ctttttctcct ttttaacaag tttaggactt cgctgccttg   960
cagagagtat tctgtatatc gaggactata taaagggat tatgccattc ataagctatg  1020
cgcatcgaca tatgtccgat tccatggttt tcttatttcc agcattattg aatatttggc  1080
tgtttagaaa aaatgcaatt aagttggttt ttttggtgct tagcgccatc taccttttct  1140
ttatcctggg aacccctatcg cgaggggcat ggttggcggt gcttatagta ggtgttctgt  1200
gggcaatact gaaccgccaa tggaagttaa taggagttgg tgccatttta ttagccatta  1260
tcggcgcttt ggttatcact caacataata acaaaccaga cccagaacat ttactgtata  1320
aattacagca gacagatagc tcatatcgtt atactaacgg aacccagggc accgcgtgga  1380
```

```
tactgattca ggaaaacccg atcaagggct acggctatgg taatgatgtg tatgatggtg    1440
tttataataa acgcgttgtc gattatccaa cgtggacctt taaagaatct atcggtccgc    1500
ataataccat tctgtacatc tggtttagtg caggcatatt gggtctggcg agcctggcct    1560
atttatatgg cgctatcatc agggaaacag ccagctctac cttcaggaaa gtagagataa    1620 gccctacaa tgctcatctc ttgctatttt tatctttcgt cggttttat atcgttcgtg       1680 gcaattttga acaggtcgat attgctcaaa ttggtatcat tactggtttt ctgttggcgc    1740
taagaaatag ataaaaaaaa cgcgctgata cttattacgg tatcagcgcg ttttccatcg    1800
tccggactca atcacttatc aaaccagctt ttcatctgtt cctcgaaacg ctgagctaca    1860
ttttcccaac tgtattttga aaacaccagg gattttgctt tttcggcaat ctggtggcgt    1920
tccttatcag caagcgcacg gttaatatca ttaattatac tgtcgctcga cataggttct    1980
gcgaggtgat agcccgttat gccatctaac acaaattcgc taatcccccc tttttgctg    2040 gcaagaaccg cttttcctgc tgccatcgct tctacagcca ccatgcaaaa tgcttcttca    2100
acctgagatg gcacaataac cagatcggct atatgataga agttatgcat ctggtcagga    2160
gattgccccc cagccataat acaatcagtt ccaatctctt tgcggcgtc cagtactttc      2220 ttttgatact ctgcttttc acccttgcgg cttgcataag gatcgccaac aacgacaagt     2280
ttaatattac ttcttaaggt acgtaatttt ttgaacgcct gcaaaagc                 2328
```

<210> SEQ ID NO 8
<211> LENGTH: 1106
<212> TYPE: DNA
<213> ORGANISM: Artificial Sequence
<220> FEATURE:
<223> OTHER INFORMATION: 3934vacDwaaL o 3934vacR

<400> SEQUENCE: 8

```
tgggatacga taaaccgcag tcgcagggcg attatgccat cgcaaaacat tttctgcatt    60
gccagcaggc ggtcagcgat ccatatgcgg tattttttaca tgccacgacc cgcgatgata   120
aacactggcc ggaagcaaac tggcgcgagc ttatcggtat ggtgggcaac accggattac    180
ggataaaact tccctggggc gcgcctcatg aggaggcccg ggctaaacga ctggccgaag    240
gctttgacta tgtggatgtg ttaccgcgca tgagcctgga ggaggtcgcc agagtgctgg    300
ctggcgcaaa atttgtcgta tcggttgata ccggcctgag ccatctcacc gccgcgctcg    360
acagaccgaa tattacgcta tatggcccaa cggaccctgg gttaattgga ggttatggga    420
agaaccaaat ggcatgctgc tcaccagaaa aaaacctggc gaatttagat gccacaagcg    480
tatttggaaa gattcattaa agagacactg tctcatccca aacctattgt ggactcgagg    540
cgctgatact tattacggta tcagcgcgtt ttccatcgtc cggactcaat cacttatcaa    600
accagctttt catctgttcc tcgaaacgct gagctacatt ttcccaactg tattttgaaa    660
acaccaggga ttttgctttt tcggcaatct ggtggcgttc cttatcagca agcgcacggt    720
taatatcatt aattatactg tcgctcgaca taggttctgc gaggtgatag cccgttatgc    780
catctaacac aaattcgcta atccccctt ttttgctggc aagaaccgct tttcctgctg     840
ccatcgcttc tacagccacc atgcaaaatg cttcttcaac ctgagatggc acaataacca    900
gatcggctat atgatagaag ttatgcatct ggtcaggaga ttgcccccca gccataatac    960
aatcagttcc aatctctttt gcggcgtcca gtactttctt ttgatactct gcttttcac     1020 ccttgcggct tgcataagga tcgccaacaa cgacaagttt aatattactt cttaaggtac    1080 gtaattttt gaacgcctgc aaaagc                                         1106
```

<210> SEQ ID NO 9
<211> LENGTH: 18
<212> TYPE: DNA
<213> ORGANISM: Artificial Sequence
<220> FEATURE:
<223> OTHER INFORMATION: oligo E

<400> SEQUENCE: 9
tgggatacga taaaccgc                                                    18

<210> SEQ ID NO 10
<211> LENGTH: 18
<212> TYPE: DNA
<213> ORGANISM: Artificial Sequence
<220> FEATURE:
<223> OTHER INFORMATION: oligo F

<400> SEQUENCE: 10
gcttttgcag gcgttcaa                                                    18

<210> SEQ ID NO 11
<211> LENGTH: 20
<212> TYPE: DNA
<213> ORGANISM: Artificial Sequence
<220> FEATURE:
<223> OTHER INFORMATION: oligo G

<400> SEQUENCE: 11
ctccgtaaca aattgaggat                                                  20

<210> SEQ ID NO 12
<211> LENGTH: 6663
<212> TYPE: DNA
<213> ORGANISM: Artificial Sequence
<220> FEATURE:
<223> OTHER INFORMATION: pKO::sb13
<220> FEATURE:
<221> NAME/KEY: misc_feature
<222> LOCATION: (608)..(608)
<223> OTHER INFORMATION: n is a, c, g, or t
<220> FEATURE:
<221> NAME/KEY: misc_feature
<222> LOCATION: (1160)..(1161)
<223> OTHER INFORMATION: n is a, c, g, or t
<220> FEATURE:
<221> NAME/KEY: misc_feature
<222> LOCATION: (1164)..(1164)
<223> OTHER INFORMATION: n is a, c, g, or t
<220> FEATURE:
<221> NAME/KEY: misc_feature
<222> LOCATION: (3072)..(3073)
<223> OTHER INFORMATION: n is a, c, g, or t
<220> FEATURE:
<221> NAME/KEY: misc_feature
<222> LOCATION: (5147)..(5147)
<223> OTHER INFORMATION: n is a, c, g, or t
<220> FEATURE:
<221> NAME/KEY: misc_feature
<222> LOCATION: (6219)..(6219)
<223> OTHER INFORMATION: n is a, c, g, or t

<400> SEQUENCE: 12
cagacgcctg ctgatgaact ggctgcaagc cgtactgccc gtgctgcggt ttttatccgt      60
aacgatccgg cgcgcccgac ccagaccggg gagctggtgg acatgctgcc ggcaccgaaa     120
ggcaaacgtt tcacgacgac tgaacagcag acgttacttt cccacggtgt ggcaacggcg    180
tatgtggaaa gcggcgtgct gcgtattcag cgggatatca cgacgtacag gaaaaatgcg    240

-continued

| | |
|---|---|
| tatggtgtgg cggataacag ctaccttgac agcgagacgc tgcataccag tgcttatgtg | 300 |
| ttgcgccgtc tgaaatctgt tattaccagt aaatacgggc gccataaact tgctaatgat | 360 |
| ggtacgcgtt tcgggtctgg tcaggccatt gtcacgcctg ccgttatccg tggtgagctg | 420 |
| ggatcaacat atcgccagat ggagcgggaa ggcatcgtgg aaaacttcga tctgttccag | 480 |
| caacatctga tagtggagcg taacgcgaac gattcgaacc gcctggatgt gctgtttccg | 540 |
| cctgattatg tcaatcagtt acgtgtgttt gcagtgctta accagttccg tctgcagtgt | 600 |
| cgaccggnga atggcgaatg ggacgcgccc tgtagcggcg cattaagcgc ggcgggtgtg | 660 |
| gtggttacgc gcagcgtgac cgctacactt gccagcgccc tagcgcccgc tcctttcgct | 720 |
| ttcttcccett cctttctcgc cacgttcgcc ggctttcccc gtcaagctct aaatcggggg | 780 |
| ctccctttag ggttccgatt tagtgcttta cggcacctcg accccaaaaa acttgattag | 840 |
| ggtgatggtt cacgtagtgg gccatcgccc tgatagacgg ttttcgccc tttgacgttg | 900 |
| gagtccacgt tctttaatag tggactcttg ttccaaactg gaacaacact caaccctatc | 960 |
| tcggtctatt cttttgattt ataagggatt ttgccgattt cggcctattg gttaaaaaat | 1020 |
| gagctgattt aacaaaaatt taacgcgaat tttaacaaaa tattaacgct tacaatttag | 1080 |
| gtggcacttt tcggggaaat gtgcgcggaa ccccctatttg tttattttc taaatacatt | 1140 |
| caaatatgta tccgctcatn ncangatcct ttttaaccca tcacatatac ctgccgttca | 1200 |
| ctattattta gtgaaatgag atattatgat attttctgaa ttgtgattaa aaaggcaact | 1260 |
| ttatgcccat gcaacagaaa ctataaaaaa tacagagaat gaaaagaaac agatagattt | 1320 |
| tttagttctt taggcccgta gtctgcaaat cctttctatga ttttctatca aacaaaagag | 1380 |
| gaaaatagac cagttgcaat ccaaacgaga gtctaataga atgaggtcga aaagtaaatc | 1440 |
| gcgcgggttt gttactgata aagcaggcaa gacctaaaat gtgtaaaggg caaagtgtat | 1500 |
| actttggcgt caccccttac atattttagg tcttttttta ttgtgcgtaa ctaacttgcc | 1560 |
| atcttcaaac aggagggctg gaagaagcag accgctaaca cagtacataa aaaggagac | 1620 |
| atgaacgatg aacatcaaaa agtttgcaaa acaagcaaca gtattaaccct ttactaccgc | 1680 |
| actgctggca ggaggcgcaa ctcaagcgtt tgcgaaagaa acgaaccaaa agccatataa | 1740 |
| ggaaacatac ggcatttccc atattacacg ccatgatatg ctgcaaatcc ctgaacagca | 1800 |
| aaaaaatgaa aaatatcaag ttcctgaatt cgattcgtcc acaattaaaa atatctcttc | 1860 |
| tgcaaaaggc ctggacgttt gggacagctg gccattacaa aacgctgacg gcactgtcgc | 1920 |
| aaactatcac ggctaccaca tcgtctttgc attagccgga gatcctaaaa atgcggatga | 1980 |
| cacatcgatt tacatgttct atcaaaaagt cggcgaaact tctattgaca gctggaaaaa | 2040 |
| cgctggccgc gtcttaaag acagcgacaa attcgatgca aatgattcta tcctaaaga | 2100 |
| ccaaacacaa gaatggtcag gttcagccac atttacatct gacggaaaaa tccgtttatt | 2160 |
| ctacactgat ttctccggta acattacgg caaacaaaca ctgacaactg cacaagttaa | 2220 |
| cgtatcagca tcagacagct cttttgaacat caacggtgta gaggattata aatcaatctt | 2280 |
| tgacggtgac ggaaaaacgt atcaaaatgt acagcagttc atcgatgaag gcaactacag | 2340 |
| ctcaggcgac aaccatacgc tgagagatcc tcactacgta aagataaag gccacaaata | 2400 |
| cttagtattt gaagcaaaca ctggaactga agatggctac caaggcgaag aatctttatt | 2460 |
| taacaaagca tactatggca aaagcacatc attcttccgt caagaaagtc aaaaacttct | 2520 |
| gcaaagcgat aaaaaacgca cggctgagtt agcaaacggc gctctcggta tgattgagct | 2580 |
| aaacgatgat tacacactga aaaagtgat gaaaccgctg attgcatcta acacagtaac | 2640 |

```
agatgaaatt gaacgcgcga acgtctttaa aatgaacggc aaatggtacc tgttcactga   2700
ctcccgcgga tcaaaaatga cgattgacgg cattacgtct aacgatattt acatgcttgg   2760
ttatgtttct aattctttaa ctggcccata caagccgctg aacaaaactg gccttgtgtt   2820
aaaaatggat cttgatccta acgatgtaac ctttacttac tcacacttcg ctgtacctca   2880
agcgaaagga aacaatgtcg tgattacaag ctatatgaca acagaggat tctacgcaga    2940 caaacaatca acgtttgcgc caagcttcct gctgaacatc aaaggcaaga aaacatctgt   3000
tgtcaaagac agcatccttg aacaaggaca attaacagtt aacaaataaa aacgcaaaag   3060
aaaatgccga tnnccggttt attgactacc ggaagcagtg tgaccgtgtg cttctcaaat   3120
gcctcaggct gtctatgtgt gactgttgag ctgtaacaag ttgtctcagg tgttcaattt   3180
catgttctag ttgctttgtt ttactggttt caccctgttct attaggtgtt acatgctgtt   3240
catctgttac attgtcgatc tgttcatggt gaacagcttt aaatgcacca aaaactcgta   3300
aaagctctga tgtatctatc ttttttacac cgtttcatc tgtgcatatg gacagttttc     3360
cctttgatat ctaacggtga acagttgttc tacttttgtt tgttagtctt gatgcttcac   3420
tgatagatac aagagccata gaacctcag atccttccgt atttagccag tatgttctct     3480
agtgtggttc gttgtttttg cgtgagccat gagaacgaac cattgagatc atgcttactt   3540
tgcatgtcac tcaaaaattt tgcctcaaaa ctggtgagct gaattttgc agttaaagca     3600 tcgtgtagtg ttttttcttag tccgttacgt aggtaggaat ctgatgtaat ggttgttggt   3660
attttgtcac cattcatttt tatctggttg ttctcaagtt cggttacgag atccatttgt   3720
ctatctagtt caacttggaa aatcaacgta tcagtcgggc ggcctcgctt atcaaccacc   3780
aatttcatat tgctgtaagt gtttaaatct ttacttattg gtttcaaaac ccattggtta   3840
agccttttaa actcatggta gttatttca agcattaaca tgaacttaaa ttcatcaagg     3900
ctaatctcta tatttgcctt gtgagttttc ttttgtgtta gttcttttaa taaccactca   3960
taaatcctca tagagtattt gttttcaaaa gacttaacat gttccagatt atattttatg   4020
aattttttta actggaaaag ataaggcaat atctcttcac taaaaactaa ttctaatttt   4080
tcgcttgaga acttggcata gtttgtccac tggaaaatct caaagccttt aaccaaagga   4140
ttcctgattt ccacagttct cgtcatcagc tctctggttg ctttagctaa tacaccataa   4200 gcatttccc tactgatgtt catcatctga gcgtattggt tataagtgaa cgataccgtc      4260
cgttctttcc ttgtagggtt ttcaatcgtg gggttgagta gtgccacaca gcataaaatt   4320
agcttggttt catgctccgt taagtcatag cgactaatcg ctagttcatt tgctttgaaa   4380
acaactaatt cagacataca tctcaattgg tctaggtgat tttaatcact ataccaattg   4440
agatgggcta gtcaatgata attactagtc ctttttccttt gagttgtggg tatctgtaaa   4500
ttctgctaga cctttgctgg aaaacttgta aattctgcta gaccctctgt aaattccgct   4560
agacctttgt gtgtttttt tgtttatatt caagtggtta taatttatag aataaagaaa   4620
gaataaaaaa agataaaaag aatagatccc agccctgtgt ataactcact actttagtca   4680
gttccgcagt attacaaaag gatgtcgcaa acgctgtttg ctcctctaca aaacagacct   4740
taaaacccta aaggcttaag tagcaccctc gcaagctcgg gcaaatcgct gaatattcct   4800
tttgtctccg accatcaggc acctgagtcg ctgtcttttt cgtgacattc agttcgctgc   4860
gctcacggct ctggcagtga atgggggtaa atggcactac aggcgccttt tatggattca   4920
tgcaaggaaa ctacccataa tacaagaaaa gcccgtcacg ggcttctcag ggcgttttat   4980
```

```
ggcgggtctg ctatgtggtg ctatctgact ttttgctgtt cagcagttcc tgccctctga    5040
ttttccagtc tgaccacttc ggattatccc gtgacaggtc attcagactg gctaatgcac    5100
ccagtaaggc agcggtatca tcaacaggct tacccgtctt actgtcngga tcgacgctct    5160
cccttatgcg actcctgcat ccctttcgtc ttcgaataaa tacctgtgac ggaagatcac    5220
ttcgcagaat aaataaatcc tggtgtccct gttgataccg ggaagccctg ggccaacttt    5280
tggcgaaaat gagacgttga tcggcacgta agaggttcca actttcacca taatgaaata    5340
agatcactac cgggcgtatt ttttgagtta tcgagatttt caggagctaa ggaagctaaa    5400
atggagaaaa aaatcactgg atataccacc gttgatatat cccaatggca tcgtaaagaa    5460
cattttgagg catttcagtc agttgctcaa tgtacctata accagaccgt tcagctggat    5520
attacggcct ttttaaagac cgtaaagaaa aataagcaca gtttatatcc ggcctttatt    5580
cacattcttg cccgcctgat gaatgctcat ccggaattcc gtatggcaat gaaagacggt    5640
gagctggtga tatgggatag tgttcaccct tgttacaccg ttttccatga gcaaactgaa    5700
acgttttcat cgctctggag tgaataccac gacgatttcc ggcagtttct acacatatat    5760
tcgcaagatg tggcgtgtta cggtgaaaac ctggcctatt tccctaaagg gtttattgag    5820
aatatgtttt tcgtctcagc caatccctgg gtgagtttca ccagttttga tttaaacgtg    5880
gccaatatgg acaacttctt cgcccccgtt ttcaccatgg caaatatta cgcaaggc     5940 gacaaggtgc tgatgccgct ggcgattcag gttcatcatg ccgtttgtga tggcttccat    6000
gtcggcagaa tgcttaatga attacaacag tactgcgatg agtggcaggg cggggcgtaa    6060 ttttttttaag gcagttattg gtgcccttaa acgcctggtg ctacgcctga ataagtgata    6120
ataagcggat gaatggcaga aattcgaaag caaattcgac ccggtcgtcg gttcagggca    6180
gggtcgttaa atagccgctt atgtctattg ctggtttant cggtacccgg gaactgtatg    6240
tcattgccgt acctgaatcc acaggcgcgg cagcaaccgt cgctttgacg gtaactggcg    6300
aagcgacgga aaccggaacg gtgaatgtct ataccggccg aacccgcgtt caggctcccg    6360
tgaccagcgg tgatgacgct gcggcggtgg ctgtgagcat taaggatgcg gtcaatgcaa    6420
accctgatct tcccttttacg gcaacatcag aagcgggggt ggtgacactg actgcgcgcc    6480
acaaggggtt atatggaaat gaaattccgg tcactctcaa ttattacggc tttggcggtg    6540
gggaggtgtt accggcgggt gtgaatatta cggttgccag cggcgtgaag ggggctggtg    6600
cgccagctct taacgacgcg gtggcagcga tgggagatga gccgttcgat tatatcgggc    6660
atc                                                                 6663
```

<210> SEQ ID NO 13
<211> LENGTH: 26
<212> TYPE: DNA
<213> ORGANISM: Artificial Sequence
<220> FEATURE:
<223> OTHER INFORMATION: oligo H

<400> SEQUENCE: 13
cccgggaact gtatgtcatt gccgta                                         26

<210> SEQ ID NO 14
<211> LENGTH: 25
<212> TYPE: DNA
<213> ORGANISM: Artificial Sequence
<220> FEATURE:
<223> OTHER INFORMATION: oligo I

<400> SEQUENCE: 14
gcatgcccga tataatcgaa cggct                                              25

<210> SEQ ID NO 15
<211> LENGTH: 25
<212> TYPE: DNA
<213> ORGANISM: Artificial Sequence
<220> FEATURE:
<223> OTHER INFORMATION: oligo J

<400> SEQUENCE: 15
gcatgcagac gcctgctgat gaact                                              25

<210> SEQ ID NO 16
<211> LENGTH: 25
<212> TYPE: DNA
<213> ORGANISM: Artificial Sequence
<220> FEATURE:
<223> OTHER INFORMATION: oligo K

<400> SEQUENCE: 16
gtcgactgca gacggaactg gttaa                                              25

<210> SEQ ID NO 17
<211> LENGTH: 49
<212> TYPE: DNA
<213> ORGANISM: Artificial Sequence
<220> FEATURE:
<223> OTHER INFORMATION: oligo L

<400> SEQUENCE: 17
ttcgattata tcgggcatgc taaaacgaaa ggctcagtcg aaagactgg                    49

<210> SEQ ID NO 18
<211> LENGTH: 28
<212> TYPE: DNA
<213> ORGANISM: Artificial Sequence
<220> FEATURE:
<223> OTHER INFORMATION: oligo M

<400> SEQUENCE: 18
ggagcatgac gtcaggaacc tcgaaaag                                           28

<210> SEQ ID NO 19
<211> LENGTH: 28
<212> TYPE: DNA
<213> ORGANISM: Artificial Sequence
<220> FEATURE:
<223> OTHER INFORMATION: oligo N

<400> SEQUENCE: 19
ctgacgtcat gctccgggcc cctaaaag                                           28

<210> SEQ ID NO 20
<211> LENGTH: 41
<212> TYPE: DNA
<213> ORGANISM: Artificial Sequence
<220> FEATURE:
<223> OTHER INFORMATION: oligo O

<400> SEQUENCE: 20
tcagcaggcg tctgcatgcc aaaaaacccc tcaagacccg t                            41

<210> SEQ ID NO 21
<211> LENGTH: 2702
<212> TYPE: DNA

<213> ORGANISM: Artificial Sequence
<220> FEATURE:
<223> OTHER INFORMATION: casete fibra

<400> SEQUENCE: 21

```
ttcgattata tcgggcatgc taaaacgaaa ggctcagtcg aaagactggg cctttcgttt      60
tataaatcta tcaccgcaag ggataaatat ctaacaccgt gcgtgttgac tattttacct     120
ctggcggtga taatggttgc atgtactaga attcattaaa gaggagaaag gtaccgcatg     180
attatgaccg gaatatttgc agaacaaact gtagaggtag ttaaaagcgc gatcgaaacc     240
gcagatgggg cattagatct ttataacaaa tacctcgacc aggtcatccc ctggaagacc     300
tttgatgaaa ccataaaaga gttaagccgt tttaaacagg agtactcgca ggaagcttct     360
gttttagttg gtgatattaa agttttgctt atggacagcc aggacaagta ttttgaagcg     420
acacaaactg tttatgaatg gtgtggtgtc gtgacgcaat actctcagc gtatatttta      480
ctatttgatg aatataatga gaaaaaagca tcagcccaga agacattct cattaggata      540
ttagatgatg gtgtcaagaa actgaatgaa gcgcaaaaat ctctcctgac aagttcacaa     600
agtttcaaca cgcttccgg aaaactgctg gcattagata gccagttaac taatgatttt      660
tcggaaaaaa gtagttattt ccagtcacag gtggatagaa ttcgtaagga agcttatgcc     720
ggtgctgcag ccggcatagt cgccggtccg tttggattaa ttatttccta ttctattgct     780
gcgggcgtga ttgaagggaa attgattcca gaattgaata caggctaaa acagtgcaa      840
aatttcttta ctagcttatc agctacagtg aaacaagcga ataaagatat cgatgcggca     900
aaattgaaat tagccactga atagcagca ttggggaga taaaaacgga aaccgaaaca      960
accagattct acgttgatta tgatgattta atgctttctt tattaaaagg agctgcaaag    1020
aaaatgatta acacctgtaa tgaataccaa caaagacacg gtaagaagac gcttttcgag    1080
gttcctgacg tcatgctccg ggcccctaaa agaagacatt ccgaaaacgg gaagcccgag    1140
accgaagcgg gaccttcccc ggctccaatc aagcgcgcca acgcatggt gagagcatcc     1200
cagcttgacc tggtttatcc tttcgattac gtggccgacc ccgtcggagg gctcaacccg    1260
ccttttttgg gtggctccgg acccctagtg gaccagggcg tcagcttac gctcaacgtc     1320
accgatccca tcatcatcaa gaacagatcg gtggacttgg cccacgaccc cagtctcgat    1380
gtcaacgccc aagtcaact ggcggtggcc gttgaccccg aagggccct ggacattacc      1440
cccgatggac tggacgtcaa ggtcgacgga gtgaccgtaa tggtcaacga tgactgggaa    1500
ctggccgtaa aagtcgaccc gtccggtgga ttggattcca ccgcgggtgg actgggggtc    1560
agcgtggacg acaccttgct cgtggatcag ggagaactgg gcgtacacct caaccaacaa    1620
ggacccatca ctgccgatag cagtggtatc gacctcgaga tcaatcctaa catgttcacg    1680
gtcaacacct cgaccggaag cggagtgctg gaactcaacc taaaagcgca gggaggcatc    1740
caagccgaca gttcgggagt gggcgttttcc gtggatgaaa gcctagagat tgtcaacaac    1800
acgctggaag tgaaaccgga tcccagcgga ccgctgacgg tctccgccaa tggcctaggg    1860
ctgaagtacg acactaatac cctagcggtg accgcgggcg ctttaaccgt ggtcggaggg    1920
gggagcgtct ccacacccat cgctacttttt gtatcgggaa gtcccagcct caacacctac    1980
aatgccacga ccgtcaattc cagcgcgaac gccttctctt gcgcctacta ccttcaacag    2040
tggaacatac aggggctcct tgttacctcc ctctacttga aattggacag cgccaccatg    2100
gggaatcgcc ctggggacct caactccgcc aatgccaaat ggttcacctt tgggtgtcc     2160
gcctatctcc agcaatgcaa ccccctccggg attcaagcgg gaacggtcag cccctccacc    2220
```

-continued

```
gccaccctca cggactttga acccatggcc aataggagcg tgaccagccc atggacgtac      2280
tcggccaatg gatactatga accatccatc ggggaattcc aagtgttcag cccggtggta      2340
acaggtgcct ggaacccggg aaacataggg atccgcgtcc tcccagtgcc ggttacggcc      2400
tctggagacc gctacaccct tctatgctac agtttgcagt gcacgaactc gagcattttt      2460
aatccagcca acagcggaac tatgatcgtg gacccgtgc tctacagctg tccagcagcc       2520
tccgtcccga agcttgcggc cgcactcgag caccaccacc accaccactg agatccggct      2580
gctaacaaag cccgaaagga agctgagttg gctgctgcca ccgctgagca ataactagca      2640
taaccccttg gggcctctaa acgggtcttg agggttttt tggcatgcag acgcctgctg       2700
at                                                                    2702
```

<210> SEQ ID NO 22
<211> LENGTH: 9331
<212> TYPE: DNA
<213> ORGANISM: Artificial Sequence
<220> FEATURE:
<223> OTHER INFORMATION: pKO::sb13-fibra
<220> FEATURE:
<221> NAME/KEY: misc_feature
<222> LOCATION: (608)..(608)
<223> OTHER INFORMATION: n is a, c, g, or t
<220> FEATURE:
<221> NAME/KEY: misc_feature
<222> LOCATION: (1160)..(1161)
<223> OTHER INFORMATION: n is a, c, g, or t
<220> FEATURE:
<221> NAME/KEY: misc_feature
<222> LOCATION: (1164)..(1164)
<223> OTHER INFORMATION: n is a, c, g, or t
<220> FEATURE:
<221> NAME/KEY: misc_feature
<222> LOCATION: (3072)..(3073)
<223> OTHER INFORMATION: n is a, c, g, or t
<220> FEATURE:
<221> NAME/KEY: misc_feature
<222> LOCATION: (5147)..(5147)
<223> OTHER INFORMATION: n is a, c, g, or t
<220> FEATURE:
<221> NAME/KEY: misc_feature
<222> LOCATION: (6219)..(6219)
<223> OTHER INFORMATION: n is a, c, g, or t

<400> SEQUENCE: 22

```
cagacgcctg ctgatgaact ggctgcaagc cgtactgccc gtgctgcggt ttttatccgt       60
aacgatccgg cgcgcccgac ccagaccggg gagctggtgg acatgctgcc ggcaccgaaa      120
ggcaaacgtt tcacgacgac tgaacagcag acgttacttt cccacggtgt ggcaacggcg     180
tatgtggaaa gcggcgtgct gcgtattcag cgggatatca cgacgtacag gaaaaatgcg    240
tatggtgtgg cggataacag ctaccttgac agcgagacgc tgcataccag tgcttatgtg    300
ttgcgccgtc tgaaatctgt tattaccagt aaatacgggc gccataaact tgctaatgat   360
ggtacgcgtt tcgggtctgg tcaggccatt gtcacgcctg ccgttatccg tggtgagctg  420
ggatcaacat atcgccagat ggagcgggaa ggcatcgtgg aaaacttcga tctgttccag  480
caacatctga tagtggagcg taacgcgaac gattcgaacc gcctggatgt gctgtttccg  540
cctgattatg tcaatcagtt acgtgtgttt gcagtgctta accagttccg tctgcagtgt  600
cgaccggnga atggcgaatg ggacgcgccc tgtagcggcg cattaagcgc ggcgggtgtg  660
gtggttacgc gcagcgtgac cgctacactt gccagcgccc tagcgcccgc tcctttcgct  720
ttcttccctt cctttctcgc cacgttcgcc ggctttcccc gtcaagctct aaatcggggg  780
```

```
ctcccctttag ggttccgatt tagtgcttta cggcacctcg accccaaaaa acttgattag    840
ggtgatggtt cacgtagtgg gccatcgccc tgatagacgg ttttcgccc tttgacgttg      900 gagtccacgt tctttaatag tggactcttg ttccaaactg gaacaacact caaccctatc    960
tcggtctatt cttttgattt ataagggatt ttgccgattt cggcctattg gttaaaaaat   1020
gagctgattt aacaaaaatt taacgcgaat tttaacaaaa tattaacgct tacaatttag   1080
gtggcacttt tcggggaaat gtgcgcggaa cccctatttg tttattttc taaatacatt    1140 caaatatgta tccgctcatn ncangatcct ttttaaccca tcacatatac ctgccgttca   1200
ctattattta gtgaaatgag atattatgat atttttctgaa ttgtgattaa aaaggcaact   1260
ttatgcccat gcaacagaaa ctataaaaaa tacagagaat gaaagaaac agatagattt    1320 tttagttctt taggcccgta gtctgcaaat cctttatga ttttctatca aacaaaagag    1380
gaaaatagac cagttgcaat ccaaacgaga gtctaataga atgaggtcga aaagtaaatc   1440
gcgcgggttt gttactgata aagcaggcaa gacctaaaat gtgtaaaggg caaagtgtat   1500
actttggcgt caccccttac atattttagg tctttttta ttgtgcgtaa ctaacttgcc    1560
atcttcaaac aggagggctg gaagaagcag accgctaaca cagtacataa aaaggagac   1620 atgaacgatg aacatcaaaa agtttgcaaa acaagcaaca gtattaacct ttactaccgc   1680
actgctggca ggaggcgcaa ctcaagcgtt tgcgaaagaa acgaaccaaa agccatataa   1740
ggaaacatac ggcatttccc atattacacg ccatgtatg ctgcaaatcc ctgaacagca    1800
aaaaaatgaa aaatatcaag ttcctgaatt cgattcgtcc acaattaaaa atatctcttc   1860
tgcaaaaggc ctggacgttt gggacagctg gccattacaa aacgctgacg gcactgtcgc   1920
aaactatcac ggctaccaca tcgtctttgc attagccgga gatcctaaaa atgcggatga   1980
cacatcgatt tacatgttct atcaaaaagt cggcgaaact tctattgaca gctggaaaaa   2040
cgctggccgc gtctttaaag acagcgacaa attcgatgca aatgattcta tcctaaaaga   2100
ccaaacacaa gaatggtcag gttcagccac atttacatct gacggaaaaa tccgtttatt   2160
ctacactgat ttctccggta acattacggg caaacaaaca ctgacaactg cacaagttaa   2220
cgtatcagca tcagacagct ctttgaacat caacggtgta gaggattata atcaatcttt   2280
tgacggtgac ggaaaaacgt atcaaaatgt acagcagttc atcgatgaag gcaactacag   2340
ctcaggcgac aaccatacgc tgagagatcc tcactacgta aagataaag gccacaaata   2400 cttagtattt gaagcaaaca ctggaactga agatggctac caaggcgaag aatctttatt   2460
taacaaagca tactatggca aaagcacatc attcttccgt caagaaagtc aaaaacttct   2520
gcaaagcgat aaaaaacgca cggctgagtt agcaaacggc gctctcggta tgattgagct   2580
aaacgatgat tacacactga aaaagtgat gaaaccgctg attgcatcta acacagtaac   2640
agatgaaatt gaacgcgcga acgtctttaa aatgaacggc aaatggtacc tgttcactga   2700
ctcccgcgga tcaaaatga cgattgacgg cattacgtct aacgatattt acatgcttgg   2760
ttatgtttct aattctttaa ctggcccata caagccgctg aacaaactg gccttgtgtt    2820 aaaaatggat cttgatccta acgatgtaac ctttacttac tcacacttcg ctgtacctca   2880
agcgaaagga aacaatgtcg tgattacaag ctatatgaca aacagaggat tctacgcaga   2940
caaacaatca acgtttgcgc caagcttcct gctgaacatc aaaggcaaga aacatctgt    3000 tgtcaaagac agcatcctttg aacaaggaca attaacagtt aacaaataaa acgcaaaag   3060 aaaatgccga tnnccggttt attgactacc ggaagcagtg tgaccgtgtg cttctcaaat   3120
gcctcaggct gtctatgtgt gactgttgag ctgtaacaag ttgtctcagg tgttcaattt   3180
```

```
catgttctag ttgctttgtt ttactggttt cacctgttct attaggtgtt acatgctgtt    3240
catctgttac attgtcgatc tgttcatggt gaacagcttt aaatgcacca aaaactcgta    3300
aaagctctga tgtatctatc ttttttacac cgttttcatc tgtgcatatg acagttttc    3360 cctttgatat ctaacggtga acagttgttc tacttttgtt tgttagtctt gatgcttcac    3420
tgatagatac aagagccata agaacctcag atccttccgt atttagccag tatgttctct    3480
agtgtggttc gttgttttg cgtgagccat gagaacgaac cattgagatc atgcttactt    3540
tgcatgtcac tcaaaaattt tgcctcaaaa ctggtgagct gaattttgc agttaaagca    3600 tcgtgtagtg ttttcttag tccgttacgt aggtaggaat ctgatgtaat ggttgttggt    3660
attttgtcac cattcatttt tatctggttg ttctcaagtt cggttacgag atccatttgt    3720
ctatctagtt caacttggaa atcaacgta tcagtcgggc ggcctcgctt atcaaccacc    3780
aatttcatat tgctgtaagt gtttaaatct ttacttattg gtttcaaaac ccattggtta    3840 agcctttaa actcatggta gttatttca agcattaaca tgaacttaaa ttcatcaagg    3900
ctaatctcta tatttgcctt gtgagttttc ttttgtgtta gttcttttaa taaccactca    3960
taaatcctca tagagtattt gttttcaaaa gacttaacat gttccagatt atattttatg    4020 aatttttta actggaaaag ataaggcaat atctcttcac taaaaactaa ttctaatttt    4080
tcgcttgaga acttggcata gtttgtccac tggaaaatct caaagccttt aaccaaagga    4140
ttcctgattt ccacagttct cgtcatcagc tctctggttg ctttagctaa tacaccataa    4200
gcatttcccc tactgatgtt catcatctga gcgtattggt tataagtgaa cgataccgtc    4260
cgttctttcc ttgtagggtt ttcaatcgtg gggttgagta gtgccacaca gcataaaatt    4320
agcttggttt catgctccgt taagtcatag cgactaatcg ctagttcatt tgctttgaaa    4380
acaactaatt cagacataca tctcaattgg tctaggtgat tttaatcact ataccaattg    4440
agatgggcta gtcaatgata attactagtc ctttttcctt gagttgtggg tatctgtaaa    4500
ttctgctaga cctttgctgg aaaacttgta aattctgcta gaccctctgt aaattccgct    4560
agacctttgt gtgtttttt tgtttatatt caagtggtta taattatag aataaagaaa    4620 gaataaaaaa agataaaag aatagatccc agccctgtgt ataactcact actttagtca    4680
gttccgcagt attacaaaag gatgtcgcaa acgctgtttg ctcctctaca aaacagacct    4740 taaaaccccta aaggcttaag tagcaccctc gcaagctcgg gcaaatcgct gaatattcct    4800
tttgtctccg accatcaggc acctgagtcg ctgtcttttt cgtgacattc agttcgctgc    4860
gctcacggct ctggcagtga atgggggtaa atggcactac aggcgccttt tatggattca    4920
tgcaaggaaa ctacccataa tacaagaaaa gcccgtcacg ggcttctcag ggcgttttat    4980
ggcgggtctg ctatgtggtg ctatctgact ttttgctgtt cagcagttcc tgccctctga    5040
ttttccagtc tgaccacttc ggattatccc gtgacaggtc attcagactg ctaatgcac    5100 ccagtaaggc agcggtatca tcaacaggct tacccgtctt actgtcngga tcgacgctct    5160
cccttatgcg actcctgcat ccctttcgtc ttcgaataaa tacctgtgac ggaagatcac    5220
ttcgcagaat aaataaatcc tggtgtccct gttgataccg ggaagccctg gccaactttt    5280
tggcgaaaat gagacgttga tcggcacgta agaggttcca actttcacca taatgaaata    5340
agatcactac cgggcgtatt ttttgagtta tcgagatttt caggagctaa ggaagctaaa    5400
atggagaaaa aaatcactgg atataccacc gttgatatat cccaatggca tcgtaaagaa    5460
cattttgagg catttcagtc agttgctcaa tgtacctata accagaccgt tcagctggat    5520
```

```
attacggcct tttaaagac cgtaaagaaa aataagcaca agttttatcc ggccttatt     5580
cacattcttg cccgcctgat gaatgctcat ccggaattcc gtatggcaat gaaagacggt   5640
gagctggtga tatgggatag tgttcaccct tgttacaccg ttttccatga gcaaactgaa   5700
acgttttcat cgctctggag tgaataccac gacgatttcc ggcagttct acacatatat    5760
tcgcaagatg tggcgtgtta cggtgaaaac ctggcctatt tccctaaagg gtttattgag   5820
aatatgtttt tcgtctcagc caatccctgg gtgagtttca ccagttttga tttaaacgtg   5880
gccaatatgg acaacttctt cgcccccgtt ttcaccatgg gcaaatatta tacgcaaggc   5940
gacaaggtgc tgatgccgct ggcgattcag gttcatcatg ccgtttgtga tggcttccat   6000
gtcggcagaa tgcttaatga attacaacag tactgcgatg agtggcaggg cggggcgtaa   6060
ttttttaag gcagttattg gtgcccttaa acgcctggtg ctacgcctga ataagtgata    6120
ataagcggat gaatggcaga aattcgaaag caaattcgac ccggtcgtcg gttcagggca   6180
gggtcgttaa atagccgctt atgtctattg ctggtttant cggtacccgg gaactgtatg   6240
tcattgccgt acctgaatcc acaggcgcgg cagcaaccgt cgctttgacg gtaactggcg   6300
aagcgacgga aaccggaacg gtgaatgtct ataccggccg aacccgcgtt caggctcccg   6360
tgaccagcgg tgatgacgct gcggcggtgg ctgtgagcat taaggatgcg gtcaatgcaa   6420
accctgatct tccctttacg gcaacatcag aagcgggggt ggtgacactg actgcgcgcc   6480
acaagggtt atatgaaat gaattccgg tcactctcaa ttattacggc tttggcggtg      6540
gggaggtgtt accggcgggt gtgaatatta cggttgccag cggcgtgaag ggggctggtg   6600
cgccagctct taacgacgcg gtggcagcga tgggagatga gccgttcgat tatatcgggc   6660
atgctaaaac gaaaggctca gtcgaaagac tgggccttc gttttataaa tctatcaccg    6720
caagggataa atatctaaca ccgtgcgtgt tgactatttt acctctggcg gtgataatgg   6780
ttgcatgtac tagaattcat taaagaggag aaaggtaccg catgattatg accggaatat   6840
ttgcagaaca aactgtagag gtagttaaaa gcgcgatcga aaccgcagat ggggcattag   6900
atctttataa caaataccct gaccaggtca tccctggaa gacctttgat gaaaccataa    6960
aagagttaag ccgttttaaa caggagtact cgcaggaagc ttctgtttta gttggtgata   7020
ttaaagtttt gcttatggac agccaggaca agtattttga agcgacacaa actgtttatg   7080
aatggtgtgg tgtcgtgacg caattactct cagcgtatat tttactattt gatgaatata   7140
atgagaaaaa agcatcagcc cagaaagaca ttctcattag gatattagat gatggtgtca   7200
agaaactgaa tgaagcgcaa aaatctctcc tgacaagttc acaaagttc aacaacgctt     7260
ccggaaaact gctggcatta gatagccagt taactaatga ttttcggaa aaaagtagtt     7320
atttccagtc acaggtggat agaattcgta aggaagctta tgccggtgct gcagccggca   7380
tagtcgccgg tccgtttgga ttaattattt cctattctat tgctgcgggc gtgattgaag   7440
ggaaattgat tccagaattg aataacaggc taaaaacagt gcaaaatttc tttactagct   7500
tatcagctac agtgaaacaa gcgaataaag atatcgatgc ggcaaaattg aaattagcca   7560
ctgaaatagc agcaattggg gagataaaaa cggaaaccga acaaccaga ttctacgttg     7620
attatgatga tttaatgctt tctttattaa aaggagctgc aaagaaaatg attaacacct   7680
gtaatgaata ccaacaaaga cacggtaaga agacgctttt cgaggttcct gacgtcatgc   7740
tccgggcccc taaaagaaga cattccgaaa acgggaagcc cgagaccgaa gcggaccttt   7800
ccccggctcc aatcaagcgc gccaaacgca tggtgagagc atcccagctt gacctggttt   7860
atcctttcga ttacgtggcc gaccccgtcg gagggctcaa cccgccttt ttgggtggct    7920
```

```
ccggacccct agtggaccag ggcggtcagc ttacgctcaa cgtcaccgat cccatcatca    7980
tcaagaacag atcggtggac ttggcccacg accccagtct cgatgtcaac gcccaaggtc    8040
aactggcggt ggccgttgac cccgaagggg ccctggacat taccccgat ggactggacg     8100 tcaaggtcga cggagtgacc gtaatggtca acgatgactg ggaactggcc gtaaaagtcg    8160
acccgtccgg tggattggat tccaccgcgg gtggactggg ggtcagcgtg acgacacct     8220 tgctcgtgga tcagggagaa ctgggcgtac acctcaacca acaaggaccc atcactgccg    8280
atagcagtgg tatcgacctc gagatcaatc ctaacatgtt cacggtcaac acctcgaccg    8340
gaagcggagt gctggaactc aacctaaaag cgcaggagg catccaagcc gacagttcgg     8400
gagtgggcgt ttccgtggat gaaagcctag agattgtcaa caacacgctg gaagtgaaac    8460
cggatcccag cggaccgctg acggtctccg ccaatggcct agggctgaag tacgacacta    8520 atacccctagc ggtgaccgcg ggcgctttaa ccgtggtcgg agggggagc gtctccacac    8580 ccatcgctac ttttgtatcg ggaagtccca gcctcaacac ctacaatgcc acgaccgtca    8640
attccagcgc gaacgccttc tcttgcgcct actaccttca acagtggaac atacaggggc    8700
tccttgttac ctccctctac ttgaaattgg acagcgccac catggggaat cgccctgggg    8760
acctcaactc cgccaatgcc aaatggttca cctttgggt gtccgcctat ctccagcaat     8820
gcaacccctc cgggattcaa gcgggaacgg tcagccccct caccgccacc ctcacggact    8880
ttgaacccat ggccaatagg agcgtgacca gcccatggac gtactcggcc aatggatact    8940
atgaaccatc catcggggaa ttccaagtgt tcagcccggt ggtaacaggt gcctggaacc    9000
cgggaaacat agggatccgc gtcctcccag tgccggttac ggcctctgga daccgctaca    9060
cccttctatg ctacagtttg cagtgcacga actcgagcat tttaatcca gccaacagcg     9120 gaactatgat cgtgggaccc gtgctctaca gctgtccagc agcctccgtc ccgaagcttg    9180
cggccgcact cgagcaccac caccaccacc actgagatcc ggctgctaac aaagcccgaa    9240
aggaagctga gttggctgct gccaccgctg agcaataact agcataaccc cttggggcct    9300
ctaaacgggt cttgaggggt ttttggcat g                                    9331
```

<210> SEQ ID NO 23
<211> LENGTH: 21
<212> TYPE: DNA
<213> ORGANISM: Artificial Sequence
<220> FEATURE:
<223> OTHER INFORMATION: oligo P

<400> SEQUENCE: 23
atcggttgat tatgcccgtc a                                              21

<210> SEQ ID NO 24
<211> LENGTH: 20
<212> TYPE: DNA
<213> ORGANISM: Artificial Sequence
<220> FEATURE:
<223> OTHER INFORMATION: oligo Q

<400> SEQUENCE: 24
caacacataa gcactggtat                                                20

<210> SEQ ID NO 25
<211> LENGTH: 1314
<212> TYPE: DNA
<213> ORGANISM: Artificial Sequence
<220> FEATURE:

<223> OTHER INFORMATION: 3934vacR

<400> SEQUENCE: 25
atcggttgat tatgcccgtc agatttgcgg tgccggaagc cagctggccc gtatggtcgg 60
ggcgtaccgt aagaccgatc catttggcga actgtatgtc attgccgtac ctgaatccac 120
aggcgcggca gcaaccgtcg ctttgacggt aactggcgaa gcgacggaaa ccggaacggt 180
gaatgtctat accggccgaa cccgcgttca ggctcccgtg accagcggtg atgacgctgc 240
ggcggtggct gtgagcatta aggatgcggt caatgcaaac cctgatcttc cctttacggc 300
aacatcagaa gcgggggtgg tgacactgac tgcgcgccac aaggggttat atggaaatga 360
aattccggtc actctcaatt attacggctt tggcggtggg gaggtgttac cggcgggtgt 420
gaatattacg gttgccagcg gcgtgaaggg ggctggtgcg ccagctctta acgacgcggt 480
ggcagcgatg ggagatgagc cgttcgatta tatcggcctt ccgtttaacg acacggcatc 540
ggtgaactcg atggcaactg aaatgaatga ttccagcggt cgctggagtt atgtccggca 600
gttgtatggt cacgtttata cggcgaagac ggggactctg tcggagcttg tggccgcggg 660
tgaccagttt aacctgcagc acatcaccct ggcgggctat gagaaagaca cccagacgcc 720
tgctgatgaa ctggctgcaa gccgtactgc ccgtgctgcg gtttttatcc gtaacgatcc 780
ggcgcgcccg acccagaccg gggagctggt ggacatgctg ccggcaccga aaggcaaacg 840
tttcacgacg actgaacagc agacgttact ttcccacggt gtggcaacgg cgtatgtgga 900
aagcggcgtg ctgcgtattc agcgggatat cacgacgtac aggaaaaatg cgtatggtgt 960
ggcggataac agctaccttg acagcgagac gctgcatacc agtgcttatg tgttgcgccg 1020
tctgaaatct gttattacca gtaaatacgg gcgccataaa cttgctaatg atggtacgcg 1080
tttcgggtct ggtcaggcca ttgtcacgcc tgccgttatc cgtggtgagc tgggatcaac 1140
atatcgccag atggagcggg aaggcatcgt ggaaaacttc gatctgttcc agcaacatct 1200
gatagtggag cgtaacgcga acgattcgaa ccgcctggat gtgctgtttc cgcctgatta 1260
tgtcaatcag ttacgtgtgt ttgcagtgct taaccagttc cgtctgcagt cgac 1314

<210> SEQ ID NO 26
<211> LENGTH: 3792
<212> TYPE: DNA
<213> ORGANISM: Artificial Sequence
<220> FEATURE:
<223> OTHER INFORMATION: 3934vacR::FIBRA (AVA-I)

<400> SEQUENCE: 26
atcggttgat tatgcccgtc agatttgcgg tgccggaagc cagctggccc gtatggtcgg 60
ggcgtaccgt aagaccgatc catttggcga actgtatgtc attgccgtac ctgaatccac 120
aggcgcggca gcaaccgtcg ctttgacggt aactggcgaa gcgacggaaa ccggaacggt 180
gaatgtctat accggccgaa cccgcgttca ggctcccgtg accagcggtg atgacgctgc 240
ggcggtggct gtgagcatta aggatgcggt caatgcaaac cctgatcttc cctttacggc 300
aacatcagaa gcgggggtgg tgacactgac tgcgcgccac aaggggttat atggaaatga 360
aattccggtc actctcaatt attacggctt tggcggtggg gaggtgttac cggcgggtgt 420
gaatattacg gttgccagcg gcgtgaaggg ggctggtgcg ccagctctta acgacgcggt 480
ggcagcgatg ggagatgagc cgttcgatta tatcgggcat gctaaaacga aaggctcagt 540
cgaaagactg ggcctttcgt tttataaatc tatcaccgca agggataaat atctaacacc 600
gtgcgtgttg actattttac ctctggcggt gataatggtt gcatgtacta gaattcatta 660

```
aagaggagaa aggtaccgca tgattatgac cggaatattt gcagaacaaa ctgtagaggt      720
agttaaaagc gcgatcgaaa ccgcagatgg ggcattagat ctttataaca aatacctcga      780
ccaggtcatc ccctggaaga cctttgatga aaccataaaa gagttaagcc gttttaaaca      840
ggagtactcg caggaagctt ctgttttagt tggtgatatt aaagttttgc ttatggacag      900
ccaggacaag tattttgaag cgacacaaac tgtttatgaa tggtgtggtg tcgtgacgca      960
attactctca gcgtatattt tactatttga tgaatataat gagaaaaaag catcagccca     1020
gaaagacatt ctcattagga tattagatga tggtgtcaag aaactgaatg aagcgcaaaa     1080
atctctcctg acaagttcac aaagtttcaa caacgcttcc ggaaaactgc tggcattaga     1140
tagccagtta actaatgatt tttcggaaaa aagtagttat ttccagtcac aggtggatag     1200
aattcgtaag gaagcttatg ccggtgctgc agccggcata gtcgccggtc cgtttggatt     1260
aattatttcc tattctattg ctgcgggcgt gattgaaggg aaattgattc agaattgaa      1320 taacaggcta aaaacagtgc aaaatttctt tactagctta tcagctacag tgaaacaagc     1380
gaataaagat atcgatgcgg caaaattgaa attagccact gaaatagcag caattgggga     1440
gataaaaacg gaaaccgaaa caaccagatt ctacgttgat tatgatgatt taatgctttc     1500
tttattaaaa ggagctgcaa agaaaatgat taacacctgt aatgaatacc aacaaagaca     1560
cggtaagaag acgcttttcg aggttcctga cgtcatgctc cgggcccta aaagaagaca      1620 ttccgaaaac gggaagcccg agaccgaagc gggaccttcc ccggctccaa tcaagcgcgc     1680
caaacgcatg gtgagagcat cccagcttga cctggtttat cctttcgatt acgtggccga     1740
ccccgtcgga gggctcaacc cgccttttt gggtggctcc ggaccctag tggaccaggg      1800 cggtcagctt acgctcaacg tcaccgatcc catcatcatc aagaacagat cggtggactt     1860
ggcccacgac cccagtctcg atgtcaacgc ccaaggtcaa ctggcggtgg ccgttgaccc     1920
cgaaggggcc ctggacatta ccccccgatgg actggacgtc aaggtcgacg gagtgaccgt     1980
aatggtcaac gatgactggg aactggccgt aaaagtcgac ccgtccggtg gattggattc     2040
caccgcgggt ggactggggg tcagcgtgga cgacaccttg ctcgtggatc agggagaact     2100
gggcgtacac ctcaaccaac aaggacccat cactgccgat agcagtggta tcgacctcga     2160
gatcaatcct aacatgttca cggtcaacac ctcgaccgga agcggagtgc tggaactcaa     2220
cctaaaagcg cagggaggca tccaagccga cagttcggga gtgggcgttt ccgtggatga     2280
aagcctagag attgtcaaca acacgctgga agtgaaaccg gatcccagcg gaccgctgac     2340
ggtctccgcc aatggcctag ggctgaagta cgacactaat accctagcgg tgaccgcggg     2400
cgctttaacc gtggtcggag gggggagcgt ctccacaccc atcgctactt ttgtatcggg     2460
aagtcccagc ctcaacaccct acaatgccac gaccgtcaat tccagcgcga acgccttctc     2520
ttgcgcctac taccttcaac agtggaacat acaggggctc cttgttacct ccctctactt     2580
gaaattggac agcgccacca tggggaatcg ccctggggac ctcaactccg ccaatgccaa     2640
atggttcacc ttttgggtgt ccgcctatct ccagcaatgc aacccctccg ggattcaagc     2700
gggaacggtc agcccctcca ccgccaccct cacggacttt gaacccatgg ccaataggag     2760
cgtgaccagc ccatggacgt actcggccaa tggatactat gaaccatcca tcggggaatt     2820
ccaagtgttc agcccggtgg taacaggtgc ctggaacccg ggaaacatag ggatccgcgt     2880
cctcccagtg ccggttacgg cctctggaga ccgctacacc cttctatgct acagtttgca     2940
gtgcacgaac tcgagcattt ttaatccagc caacagcgga actatgatcg tgggacccgt     3000
```

-continued

```
gctctacagc tgtccagcag cctccgtccc gaagcttgcg gccgcactcg agcaccacca    3060
ccaccaccac tgagatccgg ctgctaacaa agcccgaaag gaagctgagt tggctgctgc    3120
caccgctgag caataactag cataaccect tggggcctct aaacgggtct tgagggttt     3180 tttggcatgc cagacgcctg ctgatgaact ggctgcaagc cgtactgccc gtgctgcggt    3240
ttttatccgt aacgatccgg cgcgcccgac ccagaccggg gagctggtgg acatgctgcc    3300
ggcaccgaaa ggcaaacgtt tcacgacgac tgaacagcag acgttacttt cccacggtgt    3360
ggcaacggcg tatgtggaaa gcggcgtgct gcgtattcag cgggatatca cgacgtacag    3420
gaaaaatgcg tatggtgtgg cggataacag ctaccttgac agcgagacgc tgcataccag    3480
tgcttatgtg ttgcgccgtc tgaaatctgt tattaccagt aaatacgggc gccataaact    3540
tgctaatgat ggtacgcgtt tcgggtctgg tcaggccatt gtcacgcctg ccgttatccg    3600
tggtgagctg ggatcaacat atcgccagat ggagcgggaa ggcatcgtgg aaaacttcga    3660
tctgttccag caacatctga tagtggagcg taacgcgaac gattcgaacc gcctggatgt    3720
gctgtttccg cctgattatg tcaatcagtt acgtgtgttt gcagtgctta accagttccg    3780
tctgcagtcg ac                                                        3792
```